United States Patent
Funderburk

(10) Patent No.: US 8,961,610 B2
(45) Date of Patent: Feb. 24, 2015

(54) FASTENER HOLDING TOOL FOR A CRANIAL BURR HOLE PLUG

(75) Inventor: Jeffery V. Funderburk, Stevenson Ranch, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 230 days.

(21) Appl. No.: 13/614,992

(22) Filed: Sep. 13, 2012

(65) Prior Publication Data

US 2013/0066431 A1    Mar. 14, 2013

Related U.S. Application Data

(60) Provisional application No. 61/534,269, filed on Sep. 13, 2011.

(51) Int. Cl.
| | | |
|---|---|---|
| *A61F 2/02* | (2006.01) | |
| *A61F 2/28* | (2006.01) | |
| *A61N 1/05* | (2006.01) | |

(52) U.S. Cl.
CPC ............ *A61F 2/2875* (2013.01); *A61N 1/0539* (2013.01)
USPC ....................................................... 623/17.19

(58) Field of Classification Search
USPC ............ 623/17.19, 16.11; 606/129, 130, 280, 606/148, 74, 283, 281, 300; 604/175; 607/116, 139; 600/386, 429, 175
See application file for complete search history.

(56) References Cited

U.S. PATENT DOCUMENTS

| | | | |
|---|---|---|---|
| 5,927,277 | A | 7/1999 | Baudino et al. |
| 6,845,257 | B2 | 1/2005 | Fuimaono et al. |
| 6,920,359 | B2 | 7/2005 | Meadows et al. |
| 6,950,707 | B2 | 9/2005 | Whitehurst |
| 2002/0156372 | A1 | 10/2002 | Skakoon et al. |
| 2003/0028199 | A1* | 2/2003 | Ghahremani et al. ........ 606/108 |
| 2004/0122446 | A1* | 6/2004 | Solar .............................. 606/129 |
| 2009/0112327 | A1* | 4/2009 | Lane et al. ................. 623/17.19 |
| 2009/0187149 | A1 | 7/2009 | Nelson |
| 2010/0023100 | A1 | 1/2010 | Barker |
| 2013/0066410 | A1 | 3/2013 | Funderburk |
| 2013/0066430 | A1 | 3/2013 | Funderburk |

OTHER PUBLICATIONS

Axelsson, Stefan et al., Longitudinal cephalometric standards for the neurocranium in Norwegians from 6 to 21 years of age, European Journal of Orthodontics, vol. 25 (2003) pp. 185-198.

(Continued)

*Primary Examiner* — Jocelin Tanner
(74) *Attorney, Agent, or Firm* — Lowe Graham Jones PLLC; Bruce E. Black

(57) ABSTRACT

A burr hole plug comprises a plug base configured for being mounted around a burr hole. The plug base includes an aperture through which an elongated medical device exiting the burr hole may pass. The plug base is configured to accommodate a variety of cranium forms without requiring deformation of the plug base. A plug base holding tool is used to secure the plug base to the cranium, wherein the tool aligns fasteners with the plug base for insertion through the plug base and into the cranium. The burr hole plug further comprises a retainer configured for being mounted within the aperture of the plug base to secure the medical device. The retainer includes a clamping mechanism that secures the elongated medical device in the burr hole plug, wherein the movement of the clamping mechanism is controlled to prevent skewing of the clamping mechanism.

13 Claims, 19 Drawing Sheets

(56) References Cited

OTHER PUBLICATIONS

Lieberman, Daniel E. et al., Basicranial influence on overall cranial shape, Journal of Human Evolution, vol. 38 (2000) pp. 291-315.
Office Action dated Mar. 26, 2014 in U.S. Appl. No. 13/614,943, filed Sep. 13, 2012, inventor: Jeffery V. Funderburk, (18pages).
PCT International Preliminary Report on Patentability (Chapter I of the Patent Cooperation Treaty) for PCT/US2012/055212, Applicant: Boston Scientific Neuromodulation Corporation, Form PCT/IB/326 and 373, dated Mar. 27, 2014 (11pages).
PCT International Search Report for PCT/US2012/055212, Applicant: Boston Scientific Neuromodulation Corporation, Form PCT/ISA/210 and 220, dated Jul. 9, 2013 (6pages).
PCT Written Opinion of the International Search Authority for PCT/US2012/055212, Applicant: Boston Scientific Neuromodulation Corporation, Form PCT/ISA/237, dated Jul. 9, 2013 (9pages).
Communication Relating to the Results of the Partial International Search for PCT/US2012/055212, Applicant: Boston Scientific Neuromodulation Corporation, Annex Form PCT/ISA/206, dated Apr. 3, 2013 (4pages).
File History for U.S. Appl. No. 13/614,848, filed Sep. 13, 2012, Inventor: Jeffery V. Funderburk.
File History for U.S. Appl. No. 13/614,943, filed Sep. 13, 2012, Inventor: Jeffery V. Funderburk.
Office Action dated Aug. 25, 2014 in the U.S. Appl. No. 13/614,943, inventor: Jeffrey V. Funderburk, filed Sep. 13, 2012. (16pages).

* cited by examiner

FASTENER HOLDING TOOL FOR A CRANIAL BURR HOLE PLUG

RELATED APPLICATION DATA

The present application claims the benefit under 35 U.S.C. §119 to U.S. provisional patent application Ser. No. 61/534,269, filed Sep. 13, 2011. The foregoing application is hereby incorporated by reference into the present application in its entirety.

FIELD OF THE INVENTION

The present inventions relate to apparatus for securing elongated medical devices, such as catheters or leads, within a cranial burr hole.

BACKGROUND OF THE INVENTION

Deep brain stimulation (DBS) and other related procedures involving implantation of electrical stimulation leads within the brain of a patient are increasingly used to treat disorders, such as Parkinson's disease, dystonia, essential tremor, seizure disorders, obesity, depression, restoration of motor control, and other debilitating diseases via electrical stimulation via stimulation of one or more target sites, including the ventrolateral thalamus, internal segment of globus pallidus, substantia nigra pars reticulate, subthalamic nucleus (STN), or external segment of globus pallidus. DBS has become a prominent treatment option for many disorders, because it is a safe, reversible alternative to lesioning. For example, DBS is the most frequently performed surgical procedure for the treatment of advanced Parkinson's Disease. There have been approximately 30,000 patients world-wide that have undergone DBS surgery. Consequently, there is a large population of patients who will benefit from advances in DBS treatment options.

During DBS procedures, at least one burr hole is meticulously cut through the patient's cranium so as not to damage the brain tissue below, a large stereotactic targeting apparatus is mounted to the patient's cranium, and a cannula is scrupulously positioned towards the target site in the brain. A stimulation lead is then introduced through the cannula, through the burr hole, and into the parenchyma of the brain, such that one or more electrodes located on the lead are strategically placed at a target site in the brain of the patient. Once the lead is properly positioned, the portion of the lead exiting the burr hole is subcutaneously routed underneath the patient's scalp to an implantable pulse generator (IPG) implanted in the patient at a site remote from the burr hole (e.g., the patient's shoulder or chest region). Further details discussing the treatment of diseases using DBS are disclosed in U.S. Pat. Nos. 6,845,267, 6,845,267, and 6,950,707, which are expressly incorporated herein by reference.

Significantly, it is crucial that proper location and maintenance of the lead position be accomplished in order to continuously achieve efficacious therapy. This is especially so with DBS applications, in which cases, the target site (or sites) that is intended for electrical stimulation may be about the size of a pea and is located deep within the patient's brain. Thus, lead displacements of less than a millimeter may have a deleterious effect on the patient's therapy. Therefore, it is important that the electrode(s) of the lead be accurately located at the target site and that such electrode(s) be securely maintained at the target site during and after implantation of the lead.

To address these issues, a cranial burr hole plug is installed within the burr hole during the implantation procedure to hold the stimulation lead in place, as well as to seal the burr hole. Typically, the burr hole plug may be composed of a number of components, including a ring-shaped base, an insert or retainer, and a cap, that are integrated together to form the burr hole plug.

In particular, before the stimulation lead is introduced through the burr hole, the ring-shaped plug base is placed about the burr hole, and is then permanently mounted to the patient's cranium using conventional means, such as screws. The stimulation lead is then introduced through the plug base and into the parenchyma of the brain. Notably, any displacement of the portion of the lead exiting the burr hole may result in the unwanted translation of the electrodes positioned in the brain relative to the target site, thereby requiring the lead to be repositioned—a time-consuming process.

Thus, once the lead is properly located at the tissue site, the retainer is installed within the plug base (typically in an interference arrangement, such as a snap-fit arrangement) to temporarily secure the lead, thereby preventing migration of the lead relative to the target site during subsequent manipulation of the proximal end of the lead and installation of the cap. In one example, the retainer has a disk having a slot for receiving the lead and a clamping mechanism that can be rotated within the slot towards a mating surface on the disk to frictionally clamp the received lead therebetween. The clamping mechanism may have one or more locking mechanisms that can engage or disengage complementary locking mechanisms on the disk to prevent rotation of the clamping mechanism. The portion of the stimulation lead exiting the retainer can then be bent downward towards the plane of the disk into a recess formed in the plug base, and the cap can be installed onto the plug base over the retainer to permanently secure the lead within the recess. Further details regarding these types of burr hole plugs are disclosed in U.S. Patent Publication No. 2002/0156372.

It can thus be appreciated from the foregoing that the burr hole plug serves as an anchor for the implanted DBS lead as well as a cover for the entry point into the brain. Therefore, it is important for this component to be robust, well-fitting, and easy to use. Importantly, the burr hole plug should be designed such that lead does not migrate or dislodge once the lead is implanted into the brain and anchored by the burrhole plug. While prior art burr hole plugs have proven to be useful in the DBS context, there are still improvements that can be made.

As one example, the clamping mechanism used to clamp the stimulation lead should provide even pressure on the lead once the clamping mechanism is moved into position to lock the lead into place.

As another example, it is common in prior art devices for the plug base of the burr hole plug to be screwed into the burrhole in the cranium. Another design issue is that the curvature of craniums between infants and adults is different, yet the burr hole plug must be a "one-size-fits all" design. To accommodate for such differences in curvature, it is common for the burr hole plug base to be flexible, so that the burr hole plug base will bend during and after placement into the burrhole in order to conform to the shape of the cranium. However, such bending and flexing of the plug base can cause the components making up the burr hole plug to deform and stick relative to each other, thereby affecting the operation of the clamping action on the lead and, in addition, resulting in an unstable attachment of the burr hole plug to the cranium.

In yet another example, the plug base of the burr hole plug is secured to the cranium with fasteners, e.g., usually screws.

There may be flanges or wings extending from the plug base and these flanges or wings are present because they contain holes that the fasteners/screws are placed into for securing the plug base to the cranium. The use of wings or flanges extending from the plug base, however, can cause fitting challenges because, depending on the curvature of a particular cranium, the flanges or wings may not sit flush over the surface of the cranium, i.e., may be "lifted" on one part.

There, thus, remains a need for improved burr hole plug designs to address issues such as conforming the burr hole plug to different cranium shapes and. preventing skewing of the clamping mechanism used to retain the medical device in the burr hole plug.

SUMMARY OF INVENTION

In one embodiment, a cranial burr hole plug is provided. The burr hole plug includes a plug base configured for being mounted around a cranial burr hole, the burrhole plug having an aperture through which an elongated medical device exiting the burr hole may pass. The burr hole plug may also include a retainer configured for being positioned within the aperture of the plug base, the retainer having a retainer support, a slot formed in the retainer support for receiving the elongated medical device, e.g., a stimulation lead, and a clamping mechanism having a clamping bar. At least one leg extends perpendicularly from the clamping bar and is slidably engaged with the retainer support, thereby allowing the clamping bar to be slid from an open position that allows the medical device to be received in the slot to a closed position that secures the medical device within the slot. The clamping mechanism also has at least one travel stop tab respectively affixed to the at least one leg, wherein the at least one stop tab is configured for abutting the retainer support to hinder skewing of the clamping bar as the medical device is secured within the slot.

In another embodiment, the clamping mechanism is slidably mounted to the retainer support. In yet another embodiment, the clamping mechanism has a flexible locking cantilever arm coupled to the at least one leg for locking the clamping mechanism relative to the retainer support as the clamping bar is slid to the closed position. In yet another embodiment, the plug base has an annular ledge surrounding the aperture, and the retainer is configured for being positioned on the annular ledge in the plug base aperture.

In another embodiment, the burr hole plug may include a plug base having a ring-shaped body configured for being mounted around a cranial burr hole formed in a cranium, and an aperture through which an elongated medical device exiting the burr hole may pass. The ring-shaped body has an inner region and an outer region, wherein the inner region has a first contact bottom surface with a first geometry, and the outer region has a second contact bottom surface with a second geometry different from the first geometry. The first contact bottom surface of the plug base may be circular or annular. The second contact surface may be bottom contact area of a wing or lobe or, alternatively, more than one wing or lobe, extending out and part of the plug base. The burr hole plug also includes a retainer configured for being mounted within the aperture of the plug base to secure the medical device.

In one embodiment, the first bottom surface is concave and conforms to a partial sphere having a first radius, and the second bottom concave surface conforms to a sphere having a second radius. In another embodiment, the first bottom surface conforms to a partial sphere having a radius in the range of about 40-95 mm, and the second bottom surface conforms to a partial sphere having a radius in the range of about 95-140 mm. More specifically, in other embodiments, the first bottom surface conforms to a partial sphere having a radius of about 70 mm, and the second bottom surface conforms to a partial sphere having a radius of about 120 mm. In another embodiment, the inner region is an annular region, and in yet another embodiment, the outer region comprises one or more lobes.

In another embodiment of the plug base, having at least one wing or lobe, and preferably two wings or lobes extending from the plug base, the lobes have a fastener/screw hole for placing a fastener/screw through the hole and tightening the plug base to a cranium. The fastener/screw hole is placed in the lobe area to equalize pressure on the lobe as the self-tapping screw is tightened. Each one or more of the fastener holes is preferably placed at the intersection of two spheres, the spheres approximately representing the curvature of an infant's cranium and a adult sized cranium.

In an aspect of the present invention, a holding tool is provided that is used to manipulate parts of the cranial burr hole plug. The holding tool has a registration element configured for being inserted into the aperture of the burr hole plug, and a rigid collar affixed to the registration element for receiving and holding a screw/fastener. The holding tool also has a flexible receptacle including a second bore having an enlarged bore portion in which the rigid collar is positioned and a narrow bore portion in a coaxial relationship with the first bore of the rigid collar for holding and guiding the fastener/screw as it is being driven into the cranium. The narrow bore portion has a diameter/size that is slightly smaller than the largest diameter/size of the screw, typically the head of the screw, so that the narrow bore holds the screw and prevents the screw from slipping out of the narrow bore inadvertently of its own accord.

In one embodiment of the holding tool, the flexible receptacle is transparent or translucent and, in particular, the receptacle may be made of compliant silicone. In yet another embodiment, the narrow bore portion is configured to receive and maintain the fastener in position prior to applying a force to secure the burr hole plug to the cranium. In another embodiment, the tool includes one or more handles. Two handles may be used in a butterfly configuration. Each handle may be an open loop configuration and have guiding features e.g., slots molded into the handle used for guiding or stabilizing a tool, i.e., a screwdriver for engaging the screw and driving it through the plug base.

Other and further aspects and features of the invention will be evident from reading the following detailed description of the preferred embodiments, which are intended to illustrate, not limit, the invention.

BRIEF DESCRIPTION OF THE DRAWINGS

The drawings illustrate the design and utility of preferred embodiments of the present invention, in which similar elements are referred to by common reference numerals. In order to better appreciate how the above-recited and other advantages and objects of the present inventions are obtained, a more particular description of the present inventions briefly described above will be rendered by reference to specific embodiments thereof, which are illustrated in the accompanying drawings. Understanding that these drawings depict only typical embodiments of the invention and are not therefore to be considered limiting of its scope, the invention will be described and explained with additional specificity and detail through the use of the accompanying drawings in which.

DETAILED DESCRIPTION OF THE EMBODIMENTS

Figure 1:
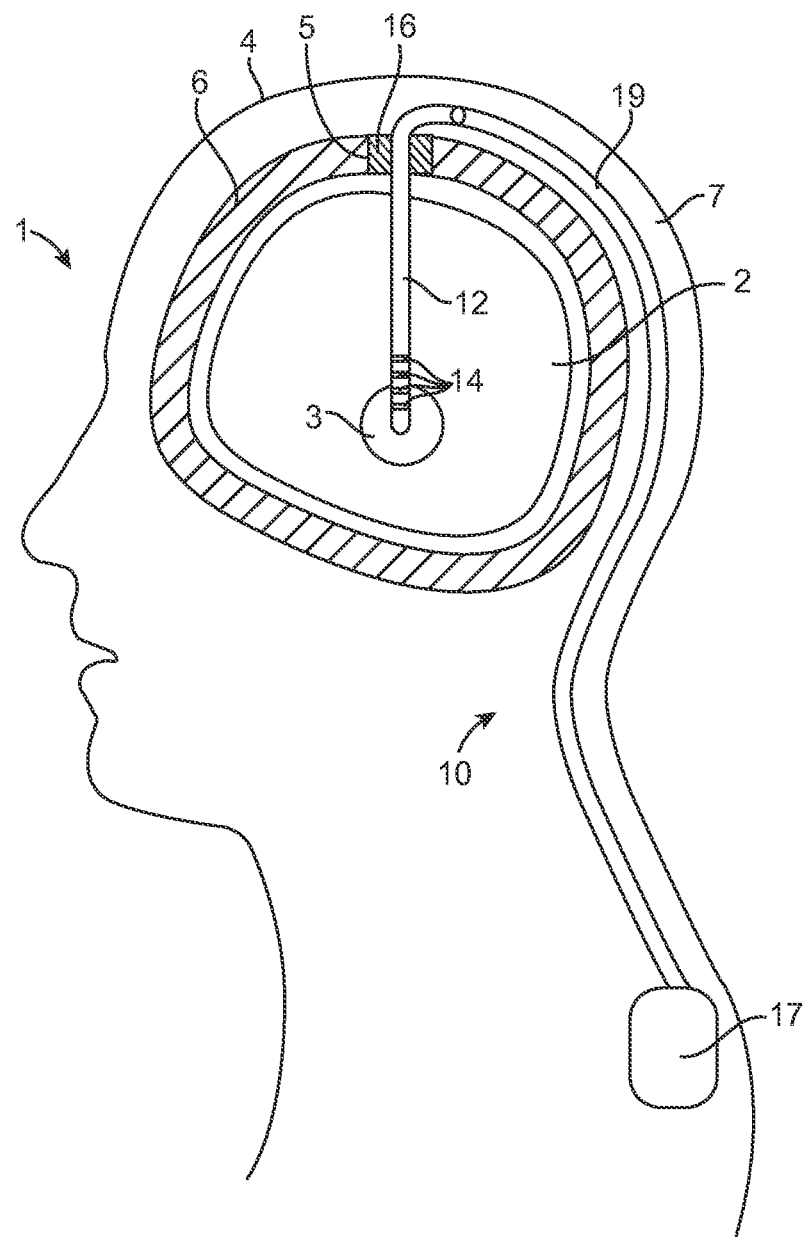
FIG. 1 is a plan view of a Deep Brain Stimulation (DBS) system constructed in accordance with one embodiment of the present inventions, wherein the DBS system is particularly shown implanted within a patient.

Turning first to FIG. 1, an exemplary DBS system 10 constructed in accordance with one embodiment of the present inventions is shown implanted within a patient for the treatment of a debilitating disease such as, Parkinson's disease, dystonia, essential tremor, seizure disorders, obesity, depression, etc. The system 10 comprises a stimulation lead 12 implanted within the parenchyma of the brain 2 of a patient 1 in order to position electrodes 14 carried by the distal end of the stimulation lead 12 adjacent a target tissue region 3, such as a deep brain structure of the patient (e.g., the ventrolateral thalamus, internal segment of globus pallidus, substantia nigra pars reticulate, subthalamic nucleus, or external segment of globus pallidus). Thus, electrical stimulation energy can be conveyed from the electrodes 14 to the target tissue region 3 to treat the disease. As can be seen, the stimulation lead 12 is introduced into the head 4 of the patient 1 via a burr hole 5 formed in the cranium 6 of the patient 1. In alternative embodiments, multiple stimulation leads (not shown) may be used, all of which may be located within the head 4 of the patient 1 via the same burr hole 5, as will be described in further detail below.

To cover the burr hole 5 and to secure the stimulation lead 12 (or leads), the system 10 further comprises a burr hole plug 16 mounted to the cranium 6 around the burr hole 5 of the patient 1. The stimulation lead 12 extends from inside the brain, through the burr hole plug 16, to a location external to the cranium 6. The structure and function of various embodiments of the burr hole plug 16 will be discussed in further detail below.

The DBS system 10 further comprises a neurostimulator 17, such as an implantable pulse generator (IPG), radio frequency (RF) receiver-stimulator, or any other device coupled to and capable of delivering electrical stimulation energy to the stimulation lead 12 in a controlled and therapeutic manner. The neurostimulator 17 is generally implanted in a surgically made pocket in the torso of the patient (e.g., the chest or abdominal region) or in other locations of the patient's body. The DBS system 10 further comprises a lead extension 19, which may be suitably connected to the proximal end of the stimulation lead 12 and subcutaneously advanced underneath the scalp 7 of the patient 1 to the neurostimulator implantation site, thereby facilitating the location of the neurostimulator 17 away from the exit point of the stimulation lead 12 (i.e., the burr hole 5). In alternative embodiments, the neurostimulator 17 may be directly implanted on or within the cranium 6 of the patient 1, as described in U.S. Pat. No. 6,920,359, which is expressly incorporated herein by reference. In this case, the lead extension 19 may not be needed. After implantation, the neurostimulator 17 is used to provide the therapeutic stimulation under control of the patient 1. The system 10 may include external components, such as a patient handheld programmer, a clinician programming station, and an external charger (all not shown), the details of which will not be described herein for purposes of brevity.

It should be understood that, while the invention lends itself well to applications in DBS, the invention in its broadest aspects may not be so limited. For example, the stimulation lead 12 (or leads) can be delivered within regions of the brain other than a deep brain structure, e.g., within or on the surface of the cerebral cortex. In addition, electrical leads, other than stimulation leads, may be delivered within the head 4 of the patient 1. For example, an electrical recording lead can be delivered into the head 4 of the patient 1 via the burr hole 5 to sense brain signals, either alone or in conjunction with a stimulation lead. Further, elongated medical devices other than electrical leads; for example, drug delivery catheters or needles, may be delivered into the head 4 of the patient 1 via the burr hole 5. Thus, it can be appreciated that the burr hole plugs described herein can be used with any elongated medical device intended to be delivered through a burr hole 5 within the cranium 6 of a patient 1 for any therapeutic and/or diagnostic purpose.

Figure 2:
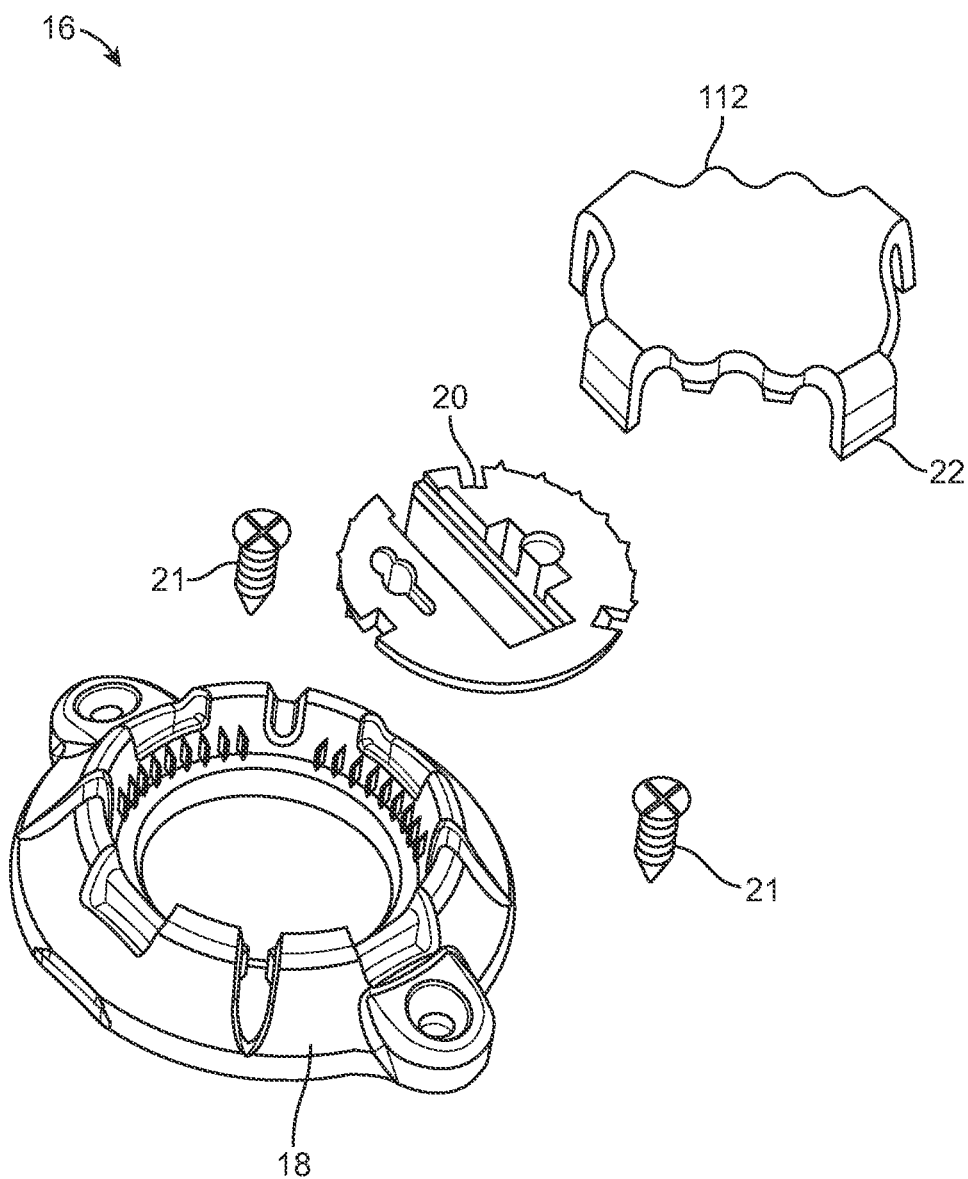
FIG. 2 is an exploded perspective view of one embodiment of a burr hole plug that can be used in the DBS system of FIG. 1.

Referring now to FIG. 2, one embodiment of a burr hole plug 16 will be described. In this embodiment, the burr hole plug 16 comprises: a plug base (or shell) 18 configured for being fixably mounted about the burr hole 5; a plurality of fasteners 21, and in this case, a pair of self-tapping screws, for mounting the plug base 18 to the cranium 6 of the patient 1; a retainer 20 configured for being positioned within the plug base 18 and for securing and retaining the stimulation lead 12 that extends through the burr hole 5; and a cap 22 configured for covering the retainer 20 and being mounted to the plug base 18 to permanently secure the stimulation lead 12 while covering the burr hole 5. The plug base 18, retainer 20, and cap 22 may be made of a suitable hard biocompatible material, such as titanium, stainless steel, alloys, hard polymers, a combination of these, or other materials that suit the function of the components therein. A less rigid material, such as silicone, may also be applied or coated to selected surface portions of one or more of the plug base 18, retainer 20, and cap 22 for improved gripping interaction between the selected surface portions.

Figure 3:
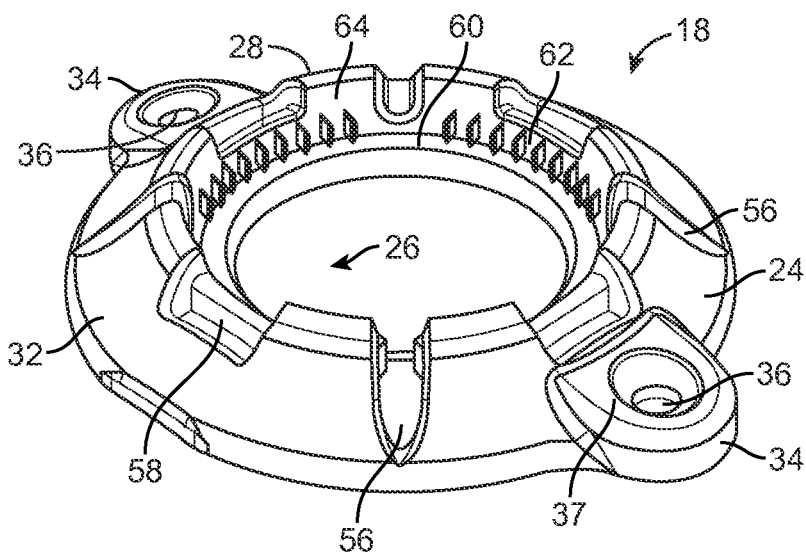
FIG. 3 is a top perspective view of a plug base that is a part of the burr hole plug of FIG. 2.
Figure 4:
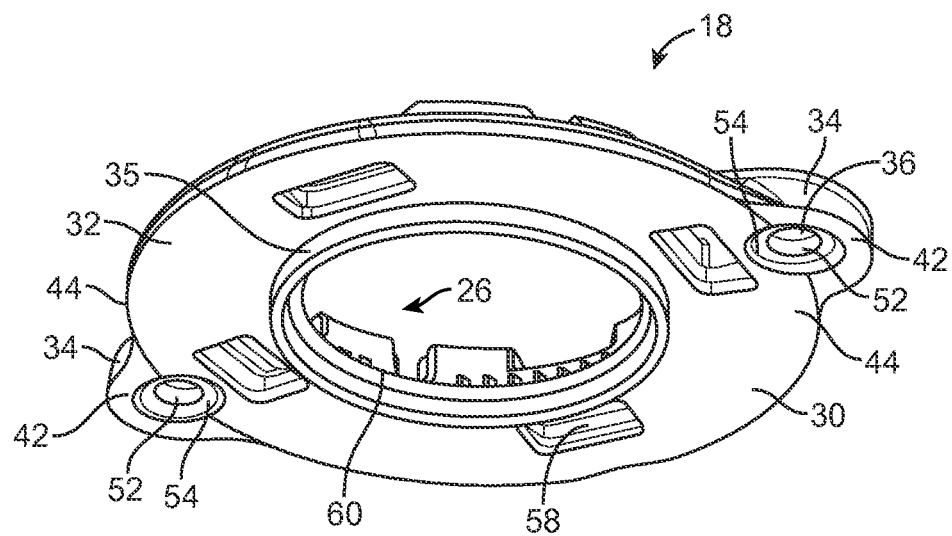
FIG. 4 is a bottom perspective view of the plug base shown in FIG. 3.
Figure 5:
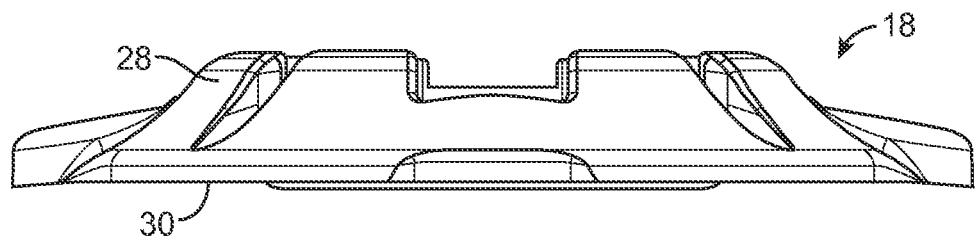
FIG. 5 is a side view of the plug base shown in FIG. 3.

Referring to FIGS. 3-5, the plug base 18 includes a closed ring-shaped body 24 and an aperture 26 through which the stimulation lead may pass. As mentioned above, the ring-shaped body 24 may be composed of a suitable hard biocompatible material, such as titanium, stainless steel, alloys, or hard polymers, and may also include a compressible material, such as silicone, on selected surface portions of the body 24 to facilitate gripping with other operational surfaces and/or by the user. The profile of the ring-shaped body 24 is preferably minimized as much as possible, such that the plug base 18 does not noticeably protrude from the cranium underneath the scalp of the patient. As best shown in FIG. 5, a top surface 28 of the ring-shaped body 24 may also be tapered to further reduce the visibility of the burr hole plug 16 below the patient's scalp. In the illustrated embodiment, a bottom surface 30 of the ring-shaped body 24 is also concave in order to conform to a typical cranium curvature. In other embodiments, the bottom surface 30 may have a concavity that is formed by inner walls defining various surface geometric shapes, e.g., conical, partly spherical or other wall shapes. As will be described in further detail below, the bottom surface 30 concavity may be formed from at least two distinguishable surfaces and also provide two contacting surfaces with the cranium: one for a first, bottom contacting surface, e.g., circular or annular, and another second contacting surface defined by the bottom of one or more wings or lobes, which contains fastener/screw holes. The first and second contacting surfaces must be carefully chosen to best conform to a range of different cranium curvatures, e.g., the cranium of an infant or the cranium of an adult so as to minimize "lift" at the wings or lobes relative to the cranium.

The outer circumference of the annular flange 35 (shown in FIG. 4) at the bottom of the plug base aperture 26 should be slightly smaller than the circumference of the burr hole 5. For example, the aperture 26 may have a circular shape and its diameter may be in the range of 10 mm to 20 mm and preferably in the range of about 8 mm to 15 mm. Thus, it can be appreciated that the ring-shaped body 24 can be disposed above the burr hole 5, such that the aperture 26 is coincident with, and lies directly above, the burr hole 5.

The plug base 18 may include an inner annular flange 35 that protrudes from the bottom surface 30 of the ring-shaped body 24 in proximity to the aperture 26. The inner annular flange 35 extends into and seats in the burr hole 5 to help align and secure the plug base 18 in the burr hole 5. Preferably, the annular flange 35 is a continuous circular flange with dimensions closely matching that of the burr hole 5, creating an interference-fit between the flange 35 and the surface of the cranium 6 forming the burr hole 5. In an alternative embodiment, instead of the inner annular flange 35, the plug base 18 comprises a plurality of self-centering tabs (not shown) protruding from the bottom surface 30 of the ring-shaped body 24 in proximity to the aperture 26 to ensure the ring-shaped body 24 is centered relative to the burr hole 5. This and other embodiments are discussed in U.S. patent application Ser. No. 12/258,382, which is expressly incorporated herein by reference.

In the illustrated embodiment, the plug base 18 is permanently secured to the cranium of the patient. To this end, the plug base 18 includes an inner region in the form of an inner annular region 32 and an outer region in the form of a pair of lobes 34 oppositely disposed on the periphery of the inner annular region 32. The plug base 18 further includes a pair of fastener holes 36 formed through an interface region 37 (shown in FIG. 3) between the inner annular region 32 and the lobes 34, which fastener/screw holes are used to receive anchoring fasteners, such as, e.g., screws, pins, spikes, tabs, or buttons. Alternatively, other means of anchoring the plug base 18 to the cranium of the patient, such as, e.g., adhesion, can be used. Gripping structures such as bumps or slight surface protrusions (not shown) may be added to the bottom surface 30 of the ring-shaped body 24 and the outer surfaces of the inner annular flange 35 to prevent rotational movement between the plug base 18 and the burr hole 5 prior to permanent anchoring to the cranium 6. Other relief structures may include, e.g., a rough sandpaper-like surface, notches, horizontal or vertical ribs or threads, etc.

The plug base 18 also has a plurality of lead exit channels 56 (in this case, four equally spaced channels) positioned on the top surface 28 of the plug base 18 that are configured for receiving a portion of the stimulation lead 12 exiting the burr hole 5. A lead 12 exiting the burr hole plug can be bent at a perpendicular angle and made parallel to the surface of the cranium 6 and seated into one of the channels 56. As will be described in further detail below, after the stimulation lead 12 is pushed into one of the channels 56, the cap 22 can be placed over to firmly secure the lead to the plug base. The presence of the lead exit channels 56 also permits a retainer holding tool inserted through the channel to allow the cap 22 to be removed from its mounted position on the plug base 18, which will also be described in further detail below.

The plug base 18 also may have a plurality of tab recesses 58 positioned on the ring-shaped body 24, which recesses extend therethrough between the top surface 28 and the bottom surface 30 of the plug base 18. In the illustrated embodiment, there are four recesses 58 that are equidistantly-positioned about the ring body 24. The tab recesses 58 in the plug base are sized and configured to receive corresponding tabs 114 (FIG. 21) on the cap 22.

The plug base 18 has an inner annular ledge 60 that creates an opening that is slightly smaller than the opening defined by the annular flange 35. The top surface of the inner annular ledge 60 in conjunction with wall or inner surface 64 (FIG. 3) provides a seat for the retainer 20 to be placed into. From this embodiment the inner annular ledge 60 prevents a stimulation lead from being abutted against the surface of sidewall of the annular flange 35. As such, having the annular ledge 60 may, by design, prevent the lead from being positioned at every possible position location within the burrhole 5 made in the cranium. The annular ledge 60 supports the retainer 20 when positioned within the aperture 26, such that an outer edge of the retainer 20 rests on the annular ledge 60, thereby preventing the retainer 20 from descending further into the burr hole 5.

The plug base 18 may also have a plurality of mechanisms that lock the retainer 20 in place while preventing, or at least hindering, rotation of the retainer 20 while it is seated into the plug base. In particular, the plug base 18 may have a plurality of base teeth 62 disposed on the inner surface 64 of the ring-shaped body 24 just above the annular ledge 60. The base teeth 62 engage complementary teeth on the retainer 20 to limit rotation of the retainer 20, and thus, prevent any inadvertent movement of the stimulation lead, as will be described in further detail below.

Figure 6:
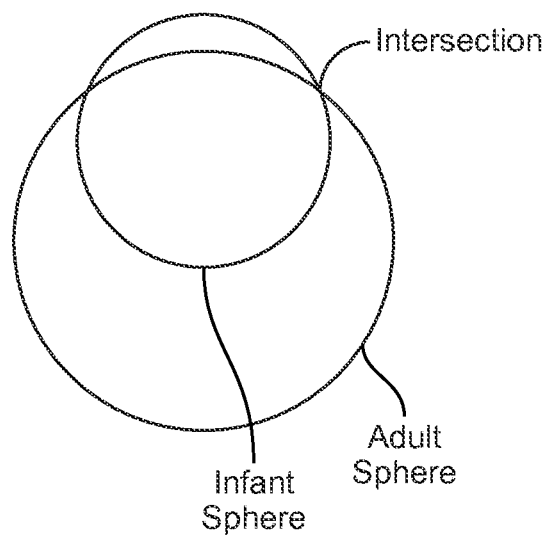
FIG. 6 is an illustration of two spheres intersecting, the smaller sphere representing an infant's cranium and the larger sphere representing an adult cranium (sizes exaggerated and out of scale for illustration purposes only)
Figure 7:
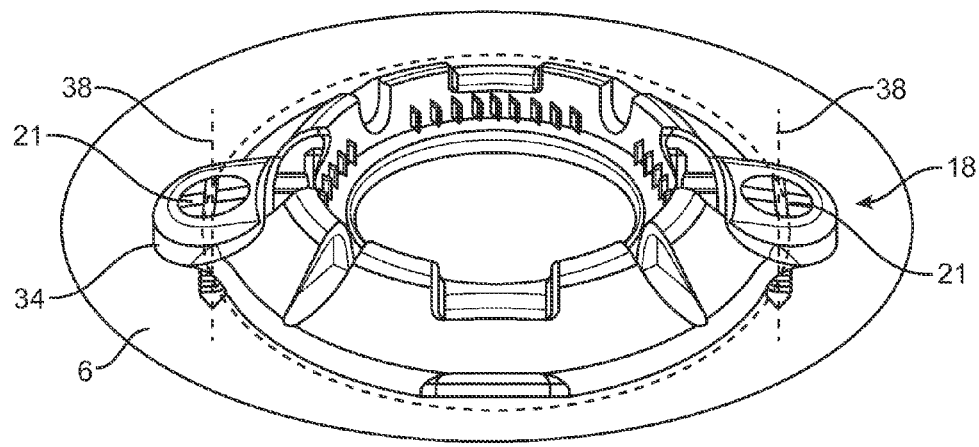
FIG. 7 is a top perspective view of the plug base shown in FIG. 3 positioned on a cranium.
Figure 8:
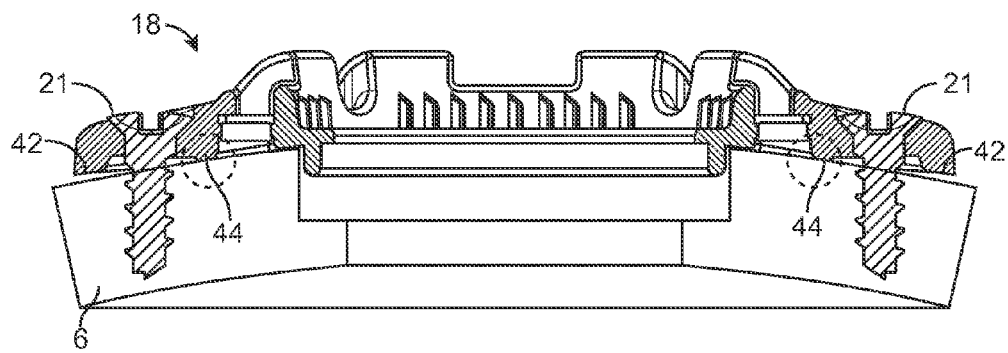
FIG. 8 is a cross-sectional view of the plug base shown in FIG. 3 positioned on a cranium having a first radius of curvature.
Figure 9:
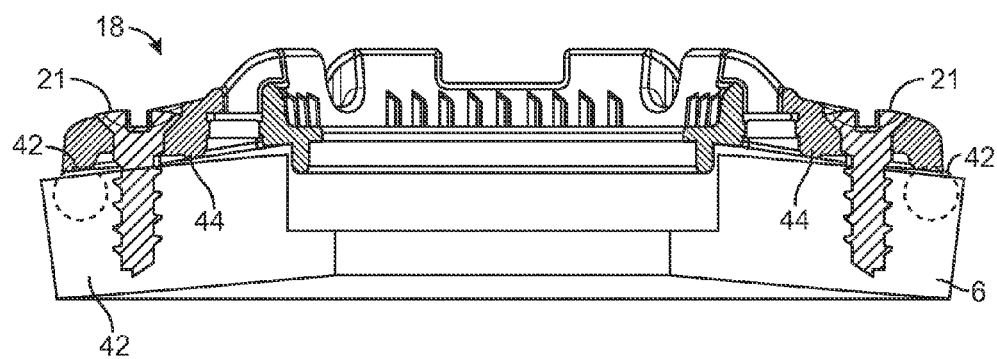
FIG. 9 is a cross-sectional view of the plug base shown in FIG. 3 positioned on a cranium having a second radius of curvature.

Referring further to FIG. 4, the lobes 34 each have a lobe outer bottom surface 42. The inner annular region 32, which is all around the plug base bottom, has a bottom annular surface 44 (shown in FIGS. 4, 8 and 9). Between the two surfaces 44 and 42, the bottom of the lobe around the fastener hole 36, there is a dead space which provides some room for bone powder/flings to collect and this feature prevents unwanted lift of the plug base or lobes from the cranium surface when the self-tapping screw extricates bone from the cranium. One of the bottom surfaces 42, 44 will always contact the cranium 6 when the plug base 18 is positioned on the cranium 6, regardless of the size of the cranium 6. It can be seen that if the cranium has a greater curvature, e.g., for an infant, the cranium will touch bottom annular surface 44, instead of lobe outer bottom surface 42. There will likely be a slight space between lobe outer bottom surface 42 and the surface of the cranium 6. For a cranium that has less curvature, e.g. an adult sized cranium, after the burrhole plug base is positioned over the cranium, the lobe outer bottom surface 42 will likely touch the surface of the cranium 6 but the bottom annular surface 44 may be lifted. One can further see that as the fastener/self tapping screw 21 is screwed into the cranium the lobe 34, which is made from material that will bend or flex without breaking, will bend and conform to the surface of the cranium so that both lobe outer bottom surface 42 and bottom annular surface 44 will be touching the cranium surface. The gap at the bottom of the fastener hole underneath the lobe will also be reduced as the self-tapping screw is screwed into the cranium. Only in the ideal case will the cranium surface touch both the bottom annular surface 44 and lobe bottom surface 42 at the outset, before the screws are tightened into the cranium. The burr hole plug base necessarily must have two bottom contacting surfaces 42 and 44 (FIGS. 8 and 9) because of need to have two lobes 34 that accommodates two fastener holes 36. Having the two separate surfaces, the lobe outer bottom surface 42 and the bottom annular surface 44, and a slightly flexible lobe 34 permits the burr hole plug base to conform to different curvatures of human cranium, from infants to adults, as well as individual curvature variations. Referring to FIG. 6, the placement of the two separate contacting surfaces is determined by their accommodation of two extreme cases of cranium curvatures, an infant and an adult. As illustration a smaller sphere (representing the infant cranium) is superimposed over an adult cranium. In the case of the infant cranium (having greater curvature), bottom annular surface 44 (FIG. 8) will touch the cranium but lobe contact surface 42 will not, before the screw is tightened into the cranium. In the case of the adult cranium, lobe bottom surface 42 (FIG. 9) will touch the cranium but not annular bottom surface 44 before the screw is driven into the cranium. The location of the screw/fastener hole must be located at the intersection of the two spheres shown in FIG. 6. When the screw is driven into the cranium, ideally both bottom annular contact surface 44 and lobe contact surface 42 will touch the surface of a cranium because of even distribution of stresses on the lobe by the screw.

In the illustrated embodiment, the bottom surfaces 42 of the lobes 34 are configured to accommodate a larger cranium, such as the cranium of an adult, and have a radius of curvature selected from a range of about 95-140 mm. The bottom annular surface 44 of the inner annular region 32 is configured to accommodate a smaller cranium, e.g., such as the cranium of a child, and has a radius of curvature selected from a range of about 40-95 mm. In an exemplary embodiment, the bottom surfaces 42 of the lobes 34 correspond to a radius of curvature of about 120 mm, and the bottom annular surface 44 of the inner annular region 32 corresponds to a radius of curvature of about 70 mm.

Because of this two separate contact surface design, when the plug base 18 is fastened to the cranium 6, initially, one of the bottom contact surfaces 42, 44 that more closely corresponds to the radius of curvature of the cranium 6 will contact the cranium 6, while the other of the bottom contact surfaces 42, 44 will be spaced slightly apart from the cranium 6 (e.g., a typical spacing from the cranium 6 may be 0.040 inch or less, and preferably approximately 0.010 inch). As one example, if the plug base 18 is fastened to a cranium having a 70 mm radius of curvature, the bottom annular contact surface 44 of the inner annular region 32 will contact the cranium 6, as shown at the circled areas of FIG. 8, while the bottom surfaces 42 of the lobes 34 will be slightly spaced from the cranium 6. In another example, if the plug base 18 is fastened to a cranium having a 120 mm curvature, the bottom surfaces 42 of the lobes 34 will contact the cranium 6, as shown at the circled areas of FIG. 9, while the bottom annular contact surface 44 of the inner annular region 32 will be slightly spaced from the cranium 6.

The plug base 18 may also be secured to a cranium 6 that has a different radius of curvature than 70 mm and 120 mm, for example, a cranium having a radius of curvature of 85 mm, or a cranium having a radius of curvature of 110 mm. The cranium 6 may also have bumps and indentations on the surface, each having a different radius of curvature than a majority of the cranium 6 surface, so it is possible that the plug base 18 is attached to a surface of the cranium 6 having different radii of curvature where such bumps and/or indentations are present. In these cases, both of the bottom contact surfaces 42, 44 may be spaced from the cranium 6 when the plug base 18 is placed on the cranium 6. This will not have a significant impact on the effectiveness of fastening the plug base 18 to the cranium 6, however, as such spacing will only be about 0.040 inch or less, and preferably approximately 0.010 inch. Also, depending on the radius of curvature of the cranium 6 and how the plug base 18 is secured to the cranium 6, it is possible that both bottom contact surfaces 42, 44 will contact the cranium 6. However, this also would not be expected to interfere with fastening the plug base 18 to the cranium 6, as it would simply result in one of the bottom contact surfaces 42, 44 being more closely pressed against the cranium 6 than the other, wherein the lessened pressure of the other of the bottom surfaces 42, 44 would mitigate any potential warping or other issue associated with the plug base 18.

It should also be noted that while the exemplary embodiment discussed above features the bottom surface 42 of the lobes 34 sized to accommodate a larger radius of curvature and the bottom annular contact surface 44 of the inner annular region 32 sized to accommodate a smaller radius of curvature, in an alternative embodiment these bottom surface geometries may be reversed. However, such reversal could result in more "lifting" of the part that does not contact the cranium 6, i.e., if the bottom surfaces 42 of the lobes 34 contact a cranium 6 having a smaller radius of curvature, the bottom annular contact surface 44 of the inner annular region 32 may be spaced farther away from the cranium 6 than with the previously-described configuration. Therefore, surface geometries that promote the bottom contact surfaces 42, 44 conforming as closely as possible to varying cranium 6 dimensions are preferred. In particular, surface geometries wherein the outermost bottom surface of the plug base 18, i.e., the bottom surfaces 42 of the lobes 34, contact the surface of the cranium 6 are preferred in order to help optimize a secure fitting of the plug base 18 to the cranium 6.

Figure 10:
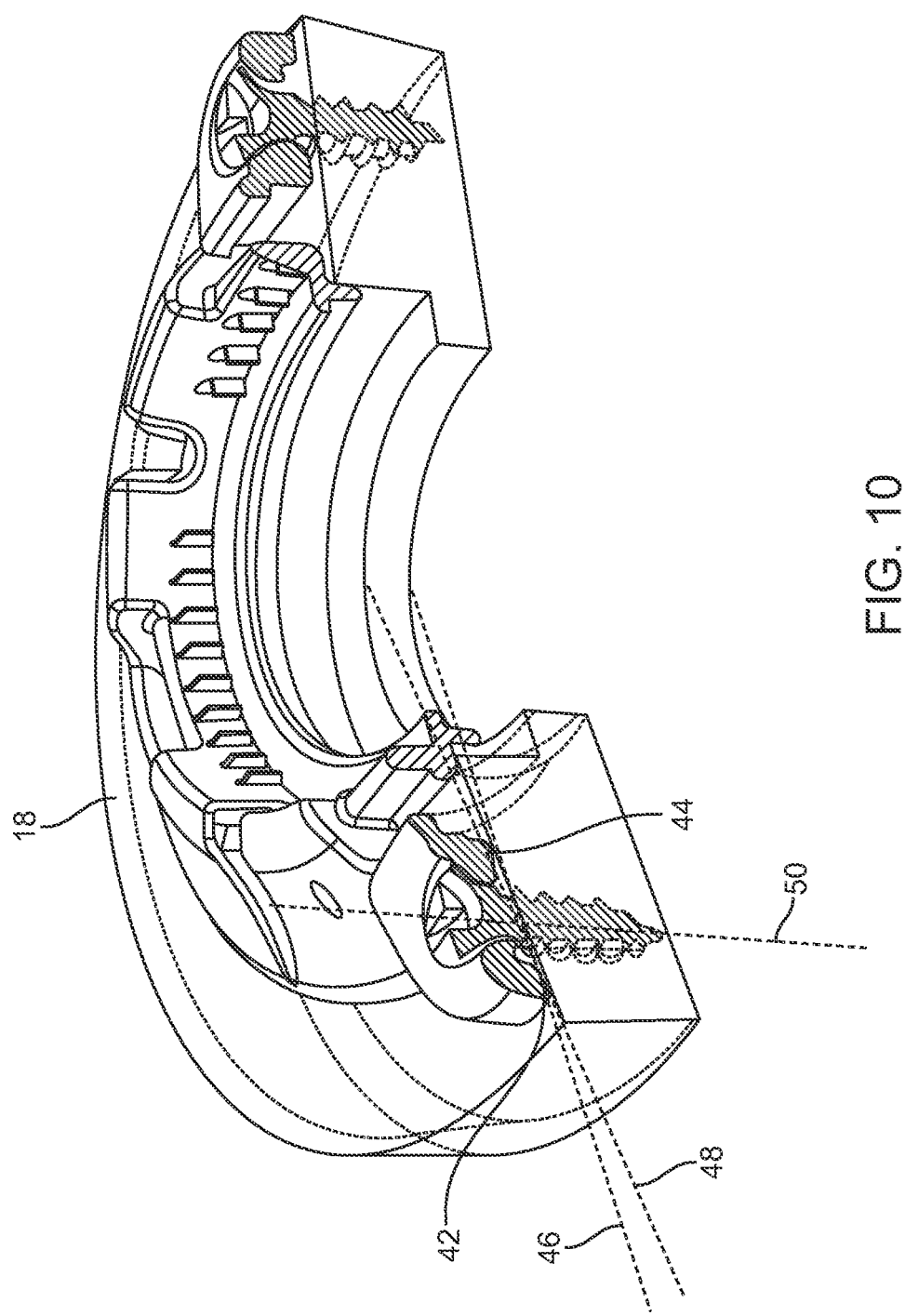
FIG. 10 is a perspective cross-sectional view of the plug base shown in FIG. 3 illustrating a cross-section of a fastener/screw inserted through the plug base.

As shown in FIG. 10, it is significant to note that a tangential plane 46 of the bottom surfaces 42 of the lobes 34 and a tangential plane 48 of the bottom surface 44 of the inner annular region 32 intersect approximately at a central longitudinal axis 38 of each fastener hole 36, as well as a central longitudinal axis 50 of the fastener 21 received in the respective fastener hole 36. In this manner, when the fastener 21 is advanced through the fastener hole 36 and the cranium 6 to secure the plug base 18 to the cranium 6, the fastener 21 applies pressure at the intersection of the tangential planes 46, 48. Thus, the pressure imparted by the fastener 21 on the plug base 18 is distributed substantially evenly between the inner annular region 32 and the lobes 34. This helps to prevent warping of or damage to the plug base 18.

In alternative embodiments, other variable geometries of the bottom surfaces 42, 44 besides radii of curvature may be employed. In one alternative embodiment, each of the bottom surfaces 42, 44 is flat and oriented on a different geometrical plane relative to the other of the bottom surfaces 42, 44. For example, the bottom surfaces 42 of the lobes 34 may be angled 15-30 degrees relative to the center of the plug base 18, and the bottom surface 44 of the inner annular region 32 may be angled 0-15 degrees relative to the center of plug base 18. In another alternative embodiment, each of the bottom surfaces 42, 44 has a combination of flat and curved surfaces. For example, an outer portion of each bottom surface 42, 44 may be flat and oriented on a different geometrical plane relative to the other of the bottom surfaces 42, 44, and a central portion of each surface 42, 44 may be concave with different or identical radii of curvature. In another alternative embodiment, each bottom surface 42, 44 forms a conical portion, and each respective conical portion lies on a different plane relative to the other conical portion. In another embodiment, an outer portion of each of the bottom surfaces 42, 44 is flat and oriented on a different geometrical plane relative to each other, and a central portion of each surface 42, 44 is conical with different or identical angular geometries. The bottom surfaces forming the cranium contact surfaces 42, 44 may also feature other geometries, such as oblong, triangular, convex, and combinations thereof, that accomplish the similar purpose of minimizing interference with the cranium 6 when the plug base 18 is placed on and secured to the cranium 6.

Because forces applied by the fastener/screw is distributed evenly, the present embodiment of the plug base prevents warping and/or incongruent mating of other components of the plug base 18. A burr hole device that has only a single bottom contact surface (and also has lobes that have fastener holes for screws) will necessarily require the lobes to unduly flex to make accommodations to various cranium curvatures. However, such single contact surface designs may be more susceptible to breaking or warping of the base plate which can interfere with the proper operation of the burrhole plug device. In the present device, the two separate bottom contact surfaces 42, 44 can better accommodate various cranium curvatures without causing warping of the plug base and also mate the plug base to the cranium surface.

Referring back to FIG. 4, to further promote effective placement of the plug base 18 on the cranium 6, an end 52 of each fastener hole 36 is surrounded by a fastener hole recess 54 (i.e., a counterbore) that is set back from the bottom surfaces 42, 44. The recesses 54 provide extra space to accommodate particulate bone chips or powder from the cranium 6 that may accumulate as the screws 21 are screwed into the cranium 6 and displace cranium 6 tissue. The screws 21 are preferably a "self-tapping" screws capable of being screwed into the cranium without pre-drilling a pilot hole into the cranium. Because the screw is self-tapping, very small particulate bone chips or powdered bone will be extricated while the screw is turned into the cranium. This bone chip matter will be stored in the space provided by fastener hole recesses 54. In other burr hole devices having a flush bottom surface with no such recess, the accumulation of bone debris may form an uneven surface on the cranium upon which the plug base may become tilted or lifted from the cranium, with the undesirable result that the plug base cannot be evenly secured to the cranium.

In an alternative embodiment of the plug base 18, the ring-shaped body 24 has an open slot (not shown) configured for laterally receiving the stimulation lead 12. The slot permits the plug base 18 to be mounted to the cranium 6 around the burr hole 5 after the stimulation lead 12 has been inserted through the burr hole 5 and into the brain tissue by simply sliding the stimulation lead 12 through the slot as the plug base 18 is moved into place. Another alternative embodiment features a split plug base having first and second annular body portions configured for being mated and demated, wherein the portions can be demated to accommodate a stimulation lead that has already been introduced through a burr hole, and then mated to integrate the plug base. In another embodiment, the ring-shaped body 24 is composed of polyetheretherketone (PEEK) material, which is durable and biocompatible polymer, as well as also MRI-compatible, or of nylon, silicone, Utlem®, Elasthane™, Tecothane®, and/or Bionate® materials. These and other alternative embodiments are described in U.S. application Ser. No. 12/258,382, which has been previously incorporated by reference.

Referring to FIGS. 11-20E, the details of the retainer 20 that retains or clamps the lead will now be described. The retainer 20 is configured for being removably positioned within the plug base aperture 26 to receive and secure the stimulation lead 12. In this regard, the retainer 20 may comprise a retainer support 65 configured for being positioned within the plug base aperture 26, and a clamping mechanism 76 mounted to the retainer support 65 and configured for applying a clamping force to the stimulation lead 12. The clamping force applied to the stimulation lead 12 may secure. the stimulation lead 12 before and while the cap 22 is being mounted to the plug base 18. The components of the retainer 20 may be composed of the same material as the plug base 18 described above, such as a hard biocompatible material, and may also include a compressible material, such as silicone, applied to selected surface portions of the retainer 20 to facilitate gripping by the user and/or with other operational surfaces.

Figure 11:
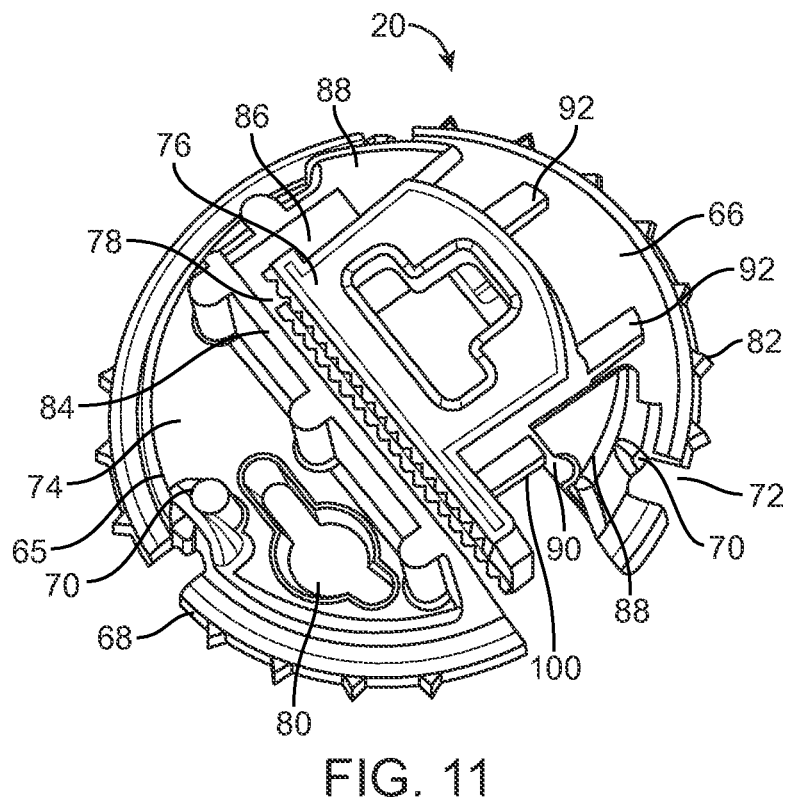
FIG. 11 is a bottom perspective view of a retainer that is part of the burr hole plug of FIG. 2.

In the illustrated embodiment, the retainer support 65 comprises a disk 66, which serves as a base for other components of the retainer 20, and an open retainer slot 79 formed in the disk 66 for receiving the stimulation lead 12, thereby allowing the retainer 20 to be positioned within the plug base aperture 26 after the stimulation lead 12 has been introduced through the burr hole 5. FIG. 11 shows the bottom side of the retainer 20. The disk 66 has an outer annular lip 68 disposed around its circumference and a thicker center portion 74 that is part of the retainer support 65, the thicker center portion preferably extends below the inner annular ledge 60 of the plug base 18 in order to provide additional stability once the retainer 20 is seated into the plug base.

Figure 13:
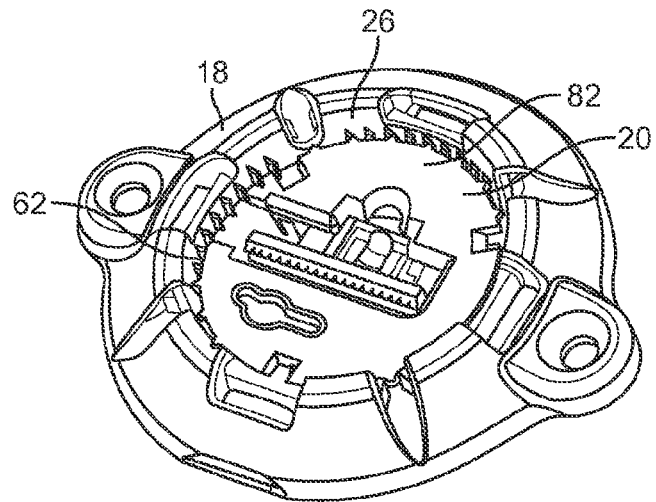
FIG. 13 is a top perspective view of the retainer of FIG. 11 positioned in the plug base shown in FIG. 3.
Figure 14:
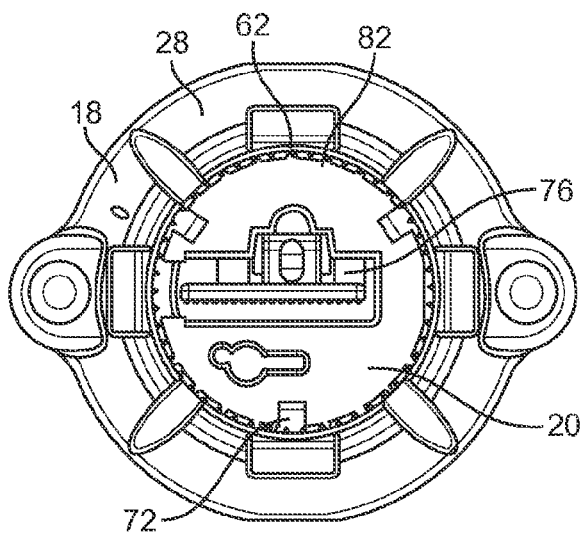
FIG. 14 is a top view of the retainer of FIG. 11 positioned in the plug base shown in FIG. 3.
Figure 15:
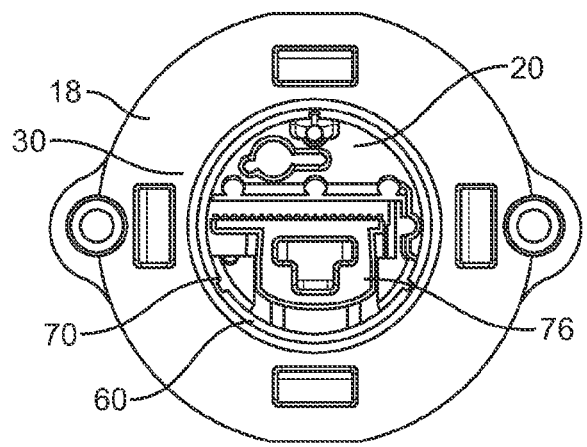
FIG. 15 is a bottom view of the retainer of FIG. 11 positioned in the plug base shown in FIG. 3.

The retainer 20 rests on top of the inner annular ledge 60 of the plug base 18 when the retainer 20 is positioned within the aperture 26 of the plug base 18, as shown in FIGS. 13-15. Specifically, the outer annular lip 68 of the retainer 20 rests on the annular ledge 60 of the plug base 18. The inner annular ledge 60 of the plug base 18 is displaced from the top edge of the plug base top surface 28 with a distance or thickness such that when the retainer 20 is seated into the plug base, the retainer does not protrude out any further than the top edge of the plug base top surface. This plug base design thus minimizes the external profile of the burr hole plug 16. At the same time, the inner annular ledge 60 prevents the retainer 20 from descending too far into the burr hole 5 or from passing through the plug base 18 and into the brain.

Figure 16:
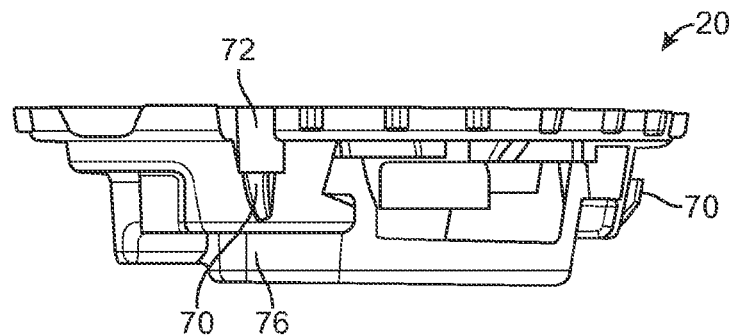
FIG. 16 is a side view of the retainer of FIG. 11.
Figure 17:
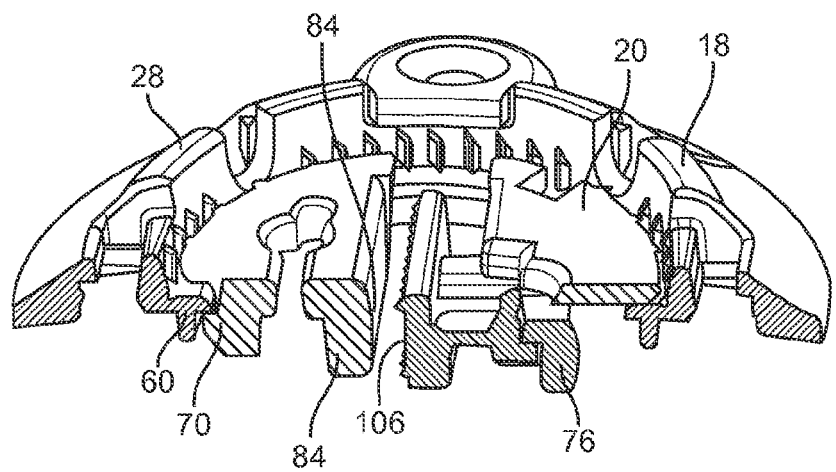
FIG. 17 is a perspective, cross-sectional view of the retainer of FIG. 11 positioned in the plug base shown in FIG. 3.

The retainer 20 is positioned in the aperture 26 of the plug base 18 such that the clamping mechanism 76 when assembled with the retainer 20 is positioned on the bottom of the retainer 20 as shown in FIG. 15, which shows the bottom of the burrhole plug base, the bottom of the retainer 20 and the clamping mechanism 76. To ensure the retainer 20 cannot be placed by a health care professional in an incorrect, upside-down placement, the retainer 20 has a plurality of snap ledges 70, readily viewed in FIG. 16, that slide over the inner annular ledge 60 of the plug base 18 as the retainer 20 is inserted in the aperture 26. The snap ledges 70 engage the annular ledge 60 once the snap ledges 70 are advanced past the annular ledge 60, as can be appreciated by FIG. 17. As the snap ledges 70 engage the inner annular ledge 60, the snap ledges 70 serve to secure the retainer 20 in the plug base 18. The snap ledges 70 are slightly tapered, as shown in FIG. 16 to allow for easier sliding of the snap ledges 70, and thus the retainer 20 to slide into the plug base 18. To this end, the retainer 20 is also slightly flexible, as the presence of the open lead slot 78 allows for slight inward flexing of the surrounding disk 66, thus allowing the snap ledges 70 to easily slide and seat the retainer 20 in the plug base 18. Each snap ledge 70 is paired with a corresponding snap ledge recess 72, wherein each snap ledge recess 72 serves as a visual marker for the position of the respective snap ledge 70. In particular, since the bottom of the retainer 20 is facing towards the brain when properly positioned in the plug base 18, the snap ledge recesses 72 indicate the position of the snap ledges 70 that are otherwise obscured from view (from top of the retainer). Locating the position of the snap ledges 70 may also be useful for removing the retainer 20 from the plug base 18 as needed.

When the snap ledges 70 engage the annular ledge 60 of the plug base 18, the ledges 70 create an audible "snap," thus providing audible feedback to the user that the retainer 20 is correctly positioned in the aperture 26. If the retainer 20 is placed upside-down, there is no such audible feedback. The snap ledges 70 also provide visible feedback, as the snap ledges 70 will be visible to the user if the retainer 20 is placed upside-down, but not if the retainer 20 is correctly placed in the plug base 18. The illustrated embodiment features three pairs of corresponding snap ledges 70 and snap ledge recesses 72, but alternative embodiments may include two pairs or four or more pairs of corresponding snap ledges 70 and snap ledge recesses 72. In other alternative embodiments, the snap ledge recesses may be replaced with grooves formed in a solid surface on the retainer 20.

As mentioned above, the retainer 20 is configured for being placed into and also for being removed from the plug base aperture 26. To this end, the retainer support 65 may include a keyhole recess 80 located on the disk 66 that may be used by a holding tool for manipulating and positioning the retainer 20. In particular, the holding tool may be inserted in the keyhole recess 80, and pulled, to disengage the retainer 20 from the plug base 20, i.e., the tool overcomes the interference fit between the snap ledges 70 and the annular ledge 60. Removal of the retainer with the tool will be described in further detail below.

Figure 12:
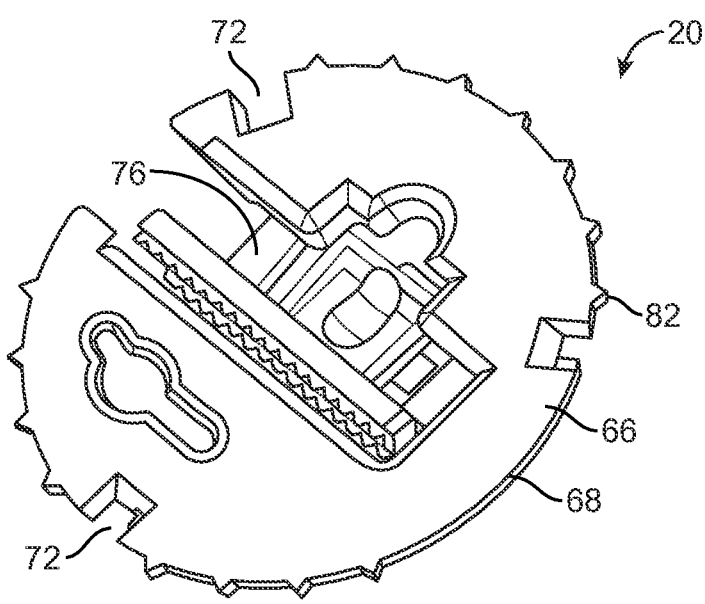
FIG. 12 is a top perspective view of the retainer shown in FIG. 11.

To prevent inadvertent rotation of the retainer 20 once it is positioned in the plug base 18, the outer annular lip 68 of the disk 66, may include a plurality of retainer teeth 82, readily viewed in FIGS. 11 and 12. The retainer teeth are configured and sized to be complementary to base teeth 62 and disposed between the base teeth 62 of the plug base 18, as shown in FIGS. 13 and 14. The retainer teeth 82 extend radially outward from the outer annular lip 68, such that the retainer teeth 82 are disposed between the base teeth 62 when the retainer 20 is positioned in the aperture 26. The retainer teeth 82 engage the base teeth 62 to hold the retainer 18 in a desired position and resist inadvertent rotation of the retainer 20 relative to the plug base. The spacing between the retainer teeth 82 and the base teeth 62 is very small once the retainer is installed into the plug base, e.g., about 2 mm or less, such that any substantial rotational movement of the retainer 20 relative to the plug base is limited. By limiting movement of the retainer 20, the corresponding teeth 62, 82 help to secure and maintain proper placement of the lead 12 when inserted in the aperture 26; otherwise, rotational movement of the retainer 20 in the plug base 18 may cause the lead 12 to shift, rotate, or even dislodge. Additionally, the corresponding teeth 62, 82 help to stabilize and limit excess rotational movement of the retainer 20 when the retainer 20 is being removed from the plug base 18, thus promoting controlled removal of the retainer 20.

In an alternative embodiment, there is only one retainer tooth 82 and two base teeth 62, wherein the retainer tooth 82 engages the base teeth 62 to hold the retainer 20 in position. In another alternative embodiment, there is only one base tooth 62 and two retainer teeth 82, wherein the retainer teeth 82 engage the base tooth 62 to hold the retainer 20 in position. In yet another embodiment, the plurality of base teeth 62 is only disposed around a portion of the inner surface 64 of the plug base 18, and in another embodiment, the plurality of retainer teeth 82 extend from only a portion of the outer annular lip 68.

The retainer support 65 includes a fixed clamping bar 84 disposed on the disk 66 adjacent one side of the lead slot 78. The fixed clamping bar 84 has a clamping surface 85 (shown in FIG. 20A) for contacting and securing the stimulation lead 12. The movable clamping mechanism 76 operates in conjunction with the fixed clamping bar 84 to secure the stimulation lead 12 therebetween, as will be described in further detail below. The retainer support 65 (shown in FIG. 11) also has a recess 86 and a pair of guide arms 88 positioned on opposite sides of the movable clamping mechanism 76. Each of the guide arms 88 has a notch-channel or groove 90 to accommodate a complementary rail 100 located on either side of the movable clamping mechanism, whereby the rail slides inside the groove for movably positioning the movable clamping mechanism 76 to into a open (release position) shown in FIG. 20C or closed (clamping position) shown in FIG. 20B.

Figure 18:
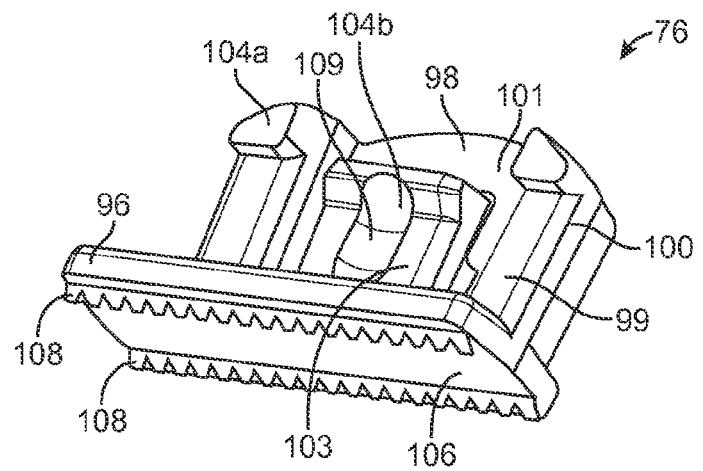
FIG. 18 is a perspective view of a clamping mechanism from the retainer of FIG. 11.
Figure 19:
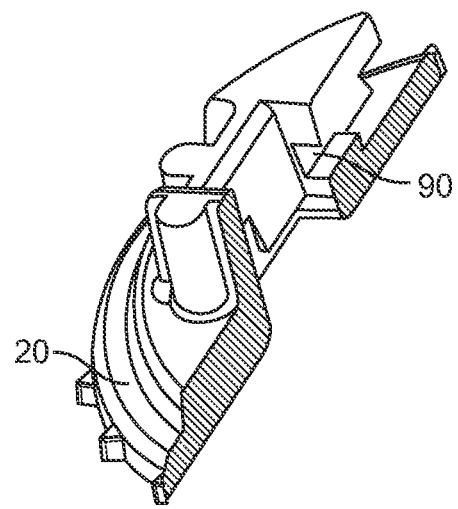
FIG. 19 is a perspective, cross-sectional view of a retainer support from the retainer of FIG. 11.

The clamping mechanism 76 is slidably engaged with the disk 66 in order to laterally slide relative to the disk 66 and clamp the stimulation lead 12 in the lead slot 78. As shown in FIG. 18, the movable clamping mechanism 76 has a movable lamping bar 96. The movable clamping bar 96 has a clamping surface 106 configured for clamping the stimulation lead 12 against the clamping surface 85 of the fixed clamping bar 84, in order to secure or release the stimulation lead 12 received within the lead slot 78. Specifically, the clamping mechanism 76 can be moved between: (a) an open position, i.e., away from the fixed clamping bar 84, which allows sufficient space to move and adjust the lead 12 in the lead slot 78, or (b) a closed position, i.e., toward the fixed clamping bar 84, wherein the lead 12 is clamped in a selected position with a force defined by the fixed distance of the lead slot 78. In one embodiment, the maximum travel of the movable clamping mechanism 76 is limited so that its clamping surface 85 cannot physically reach and touch the clamping surface 85 of the fixed clamping bar 84 Indeed, the width of the lead slot 78 will be determined by the diameter of the stimulation lead 12 intended to be clamped so that it will not be possible to overclamp and cause damage to the stimulation lead. Once the stimulation lead is clamped, the cross-section of the lead 12 will no longer be a circle, but will be flatter, resembling an ovoid, as shown in.

The movable clamping mechanism 76 also includes an operating element 98 (shown in FIG. 18) that is coupled to the clamping bar 96 and used to selectively slide the clamping bar 96 between the open and closed positions. In the illustrated embodiment, the operating element 98 includes one or more legs 99 extending perpendicularly from the movable clamping bar 96 away from the lead slot 78 and one or more rails 100 (or tongue) that extend along the outer surface of the legs 99. In the illustrated embodiment, there are two legs 99 and two rails 100. The sliding arrangement between the clamping mechanism 76 and the disk 66 is provided between the rails 100 moving in cooperation with the guide arms 88. In particular, the rails 100 are slidably received within the notch-channels 90 of the guide arms 88 in a closely-toleranced relationship, so that the operating element 98 and the movable clamping bar 96 coupled thereto can be smoothly moved back and forth in a lateral direction (i.e., perpendicular to the lead slot 78 and the fixed clamping bar 84. In the illustrated embodiment, the operating element 98 includes a U-shaped flange 101 extending between the legs 99. In other embodiments, as examples, the operating element 98 includes a T-shaped structure, wherein the center of the T extends from the movable clamping bar 96 and the top of the T extends between the legs 99, or a bar extending between the legs 99, or there may be no additional structure between the legs 99.

The inner, flat portions of the guide arms 88 are tapered slightly inwardly as they approach towards the fixed clamping bar. As a result, as the clamping mechanism is slid toward the clamping position, the surface of the legs 99 (FIG. 18) begin to contact the flat surface of the guide arms 88 (FIG. 11), much like a wedge. This wedge action causes the clamping mechanism 76 to become tight and fixed, as it approaches the clamping position. In other words, the inward tapering of the two guide arms 88 reduces the width of the space through which the clamping mechanism 76 laterally moves toward the closed position. This helps to control residual movement and prevents skewing of the clamping mechanism 76 in the clamped position.

Figure 20A:
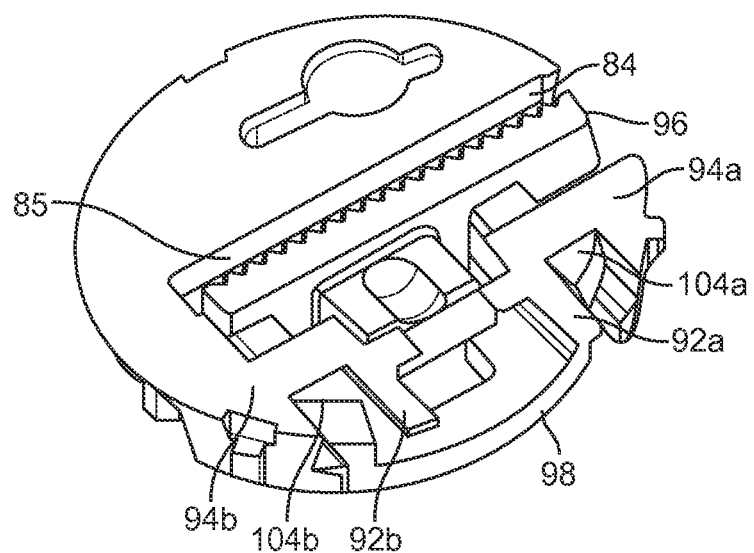
FIG. 20A is a top perspective view of a clamping mechanism from FIG. 18 in the retainer of FIG. 11 in a closed position.

To further control movement of the movable clamping mechanism 76, the disk 66 has a pair of parallel base rails 92 (FIG. 20A) thereon that are each adjacent to an inner surface of one of the legs 99 of the operating element 98. The base rails 92 contact the legs 99 to guide the operating element 98 to move substantially in a straight path. The base rails 92a, 92b also have stop ledges 94a, 94b, respectively, extending perpendicularly therefrom toward the outer annular lip 68 of the disk 66, The stop ledges 94 engage stop tabs 104a, 104b protruding from the legs 99 of the operating element 98, as best seen in FIG. 20A.

When the operating element 98 slides in the notch-channels 90 to advance the clamping mechanism 76 toward the closed position, one or both of the stop tabs 104a, 104b abuts one or both of the corresponding stop ledges 94. This limits the movement of the clamping mechanism 76 toward the closed, clamped position, i.e., movement of the movable clamping bar 96 toward the fixed clamping bar 84. Also, the stop tabs 104a, 104b prevent undue skewing of the movable clamping bar 96, since at least one end of the movable clamping bar 96 will be prevented from moving too far towards the fixed clamping bar 84. This is accomplished because at least one, or in some cases, both stop tabs 104a, 104b will abut the corresponding stop ledges 94a or 94b, before the clamping mechanism can over-travel and damage a stimulation lead. It will often be the case that one stop tab will be touching the corresponding stop ledge, but the other stop tab and corresponding stop ledge will not be touching in the fully clamped position. This is because the stimulation lead will, in many cases, not be clamped near the center of the fixed clamping surface 85 and movable clamping bar 96, but instead near one end or the other end of the movable clamping bar.

Figure 20B:
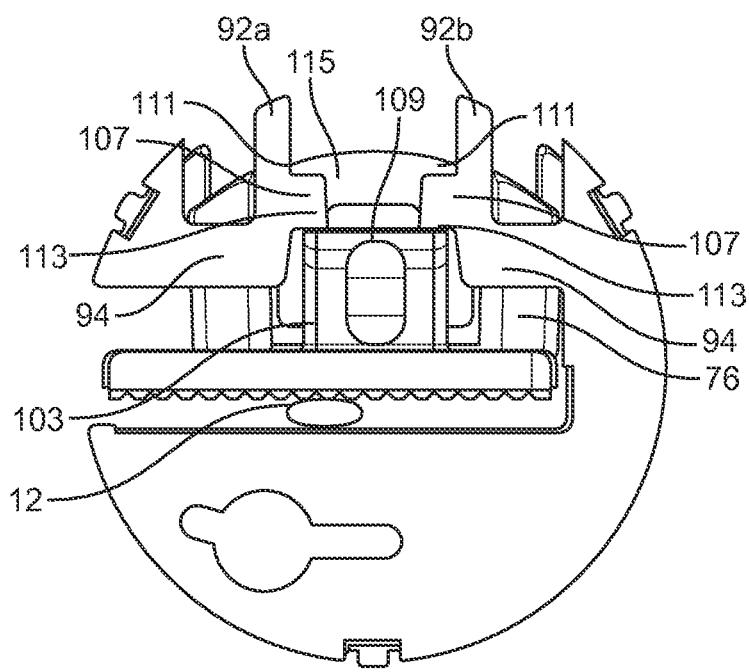
FIG. 20B is a top view of the clamping mechanism from FIG. 18 in the retainer of FIG. 11 in a closed position and also showing a planar section of the retainer.
Figure 20C:
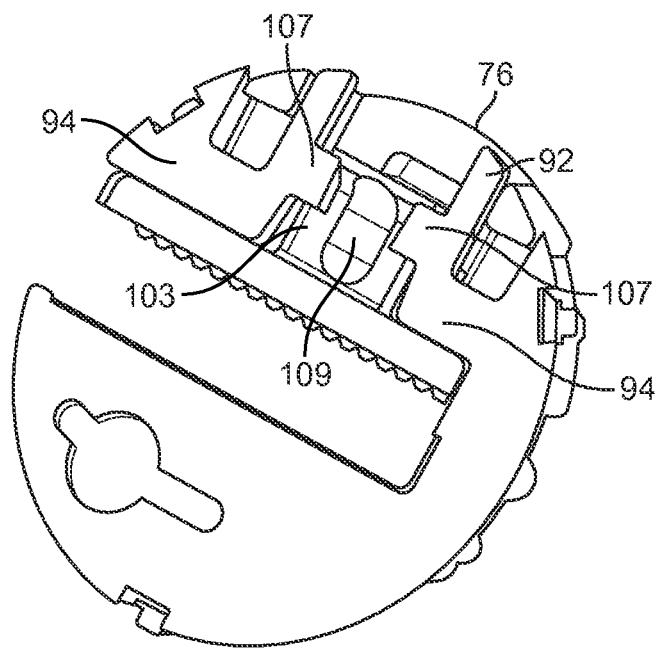
FIG. 20C is a top perspective view of the clamping mechanism from FIG. 18 in the retainer of FIG. 11 in an open position and also showing a planar section of the retainer.
Figure 20D:
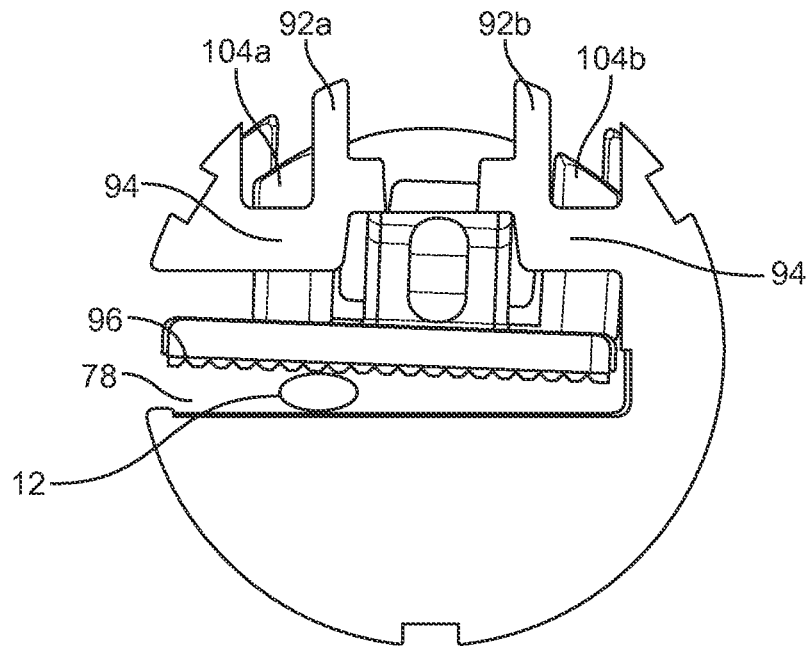
FIG. 20D is a bottom view of the clamping mechanism from FIG. 18 in the retainer of FIG. 11 showing the skewing that occurs between clamping surfaces as the clamping mechanism is pushed closed.
Figure 20E:
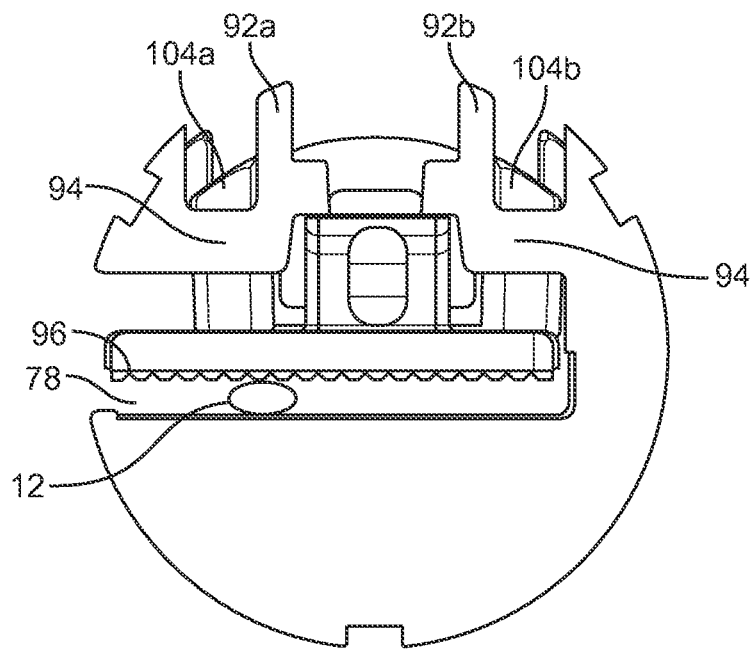
FIG. 20E is a bottom view of the clamping mechanism from FIG. 18 in the retainer of FIG. 11 showing the skewing that lessens between clamping surfaces as the lead becomes fully clamped.

To illustrate, FIG. 20D shows one stop tab 104b contacting one of the stop ledges 94 while the other stop tab 104a is spaced from the other stop ledge 94. The stop ledge 94 abutting the stop tab 104b thus prevents the clamping mechanism 76 from moving too far toward the fixed clamping bar 84 in a skewed configuration. Also, the portion of the operating element 98 where the other stop tab 104a is positioned can be moved further toward the lead 12 and the fixed clamping bar 84 to position the movable clamping bar 96 more closely parallel to the fixed clamping bar 84 to more evenly secure the lead 12, as shown in FIG. 20E.

The clamping mechanism 76 also has a resilient locking cantilever arm 103, as shown in FIGS. 18, 20B and 20C, extending perpendicularly from the movable clamping bar 96 between the legs 99 of the operating element 98. The cantilever arm 103 is only attached to the movable clamping bar and can be pressed down relative to the legs 99 and operating element 98. When the clamp is fully closed, the cantilever arm is snapped into a position that abuts against the locking ledges 107 at surfaces 113. This is a completely locked, fully clamped position. FIG. 20C shows the unlocked or open position of the clamp. A pair of locking ledges 107 each extend perpendicularly from one of the base rails 92a, 92b (FIGS. 11 and 20C) of the retainer support 65, as shown in FIG. 20B. In an alternative embodiment, the cantilever arm 103 does not feature a locking element but instead has a tapered surface to engage a corresponding locking element, such as the locking ledges 107.

The locking ledges 107 extend in a direction opposite that of the stop ledges 94 on the respective base rails 92 and have first and second locking ledge surfaces 111, 113 oriented perpendicular to the movement direction of the clamping mechanism 76 and located in opposing sides on the locking ledges 107. By pressing the cantilever arm downwards at operating recess 109 and concurrently also applying force, pointing away from the center of the disc 66, the clamping mechanism 76 moves toward the open position, and the cantilever arm 103 flexes to pass over and engage the locking ledges 107 at first surface 111, as shown in FIG. 20C, causing the clamping mechanism 76 to be locked in the open position. The clamping mechanism 76 can be unlocked by pressing down at operating recess 109 and pushing to the clamping or closed position flexing the cantilever arm 103 to disengage the arm 103 from the locking ledges 107.

Also, referring to FIG. 20B, as the clamping mechanism 76 moves toward the closed position, the cantilever arm 103, and in particular a cantilever arm contact surface 115 of the cantilever arm 103, engages the locking ledge second surfaces 113 of the locking ledges 107, such that the clamping mechanism 76 is maintained in the closed position to help secure the lead 12. The clamping mechanism 76 can be unlocked by flexing the cantilever arm 103 for disengagement from locking ledges 107 and sliding the operating element 98, and thus, the movable clamping bar 96, away from the fixed clamping bar 84 to the open position.

The cantilever arm 103 has an operating recess 109 formed on the arm 103 for receiving a tool that can be used to flex the arm 103 to disengage the arm 103 from the locking ledges 107. The tool can also be received within the recess 109 to slide the movable clamping bar 96 toward the closed or open position. In particular, a retainer holding tool may be used for flexing the resilient arm 103 and sliding the movable clamping bar 96, as will be described in further detail below.

As mentioned above, the movable clamping bar 96 has a clamping surface 106 that faces and extends parallel to the fixed clamping surface 85 of the fixed clamping bar 84, as viewed in FIG. 20A, such that the lead 12 is clamped between the clamping surfaces 106 (FIG. 18), and fixed clamping surface 85, as shown in FIG. 20B. To this end, the clamping surface 106 of the movable clamping bar 96 has one or more rows of clamping teeth 108, as viewed in FIG. 18, extending in a top row and a bottom row across the entire length of the movable clamping bar 96. In alternative embodiments, the clamping surface 106 has one row of clamping teeth 108, or more than two rows of clamping teeth 108 across the entire or partial length of the movable clamping bar 96. The clamping teeth 108 grip and hold the lead 12 securely in the lead slot 78 by preventing lateral, vertical, and rotational movement of the lead 12, thus helping to maintain the desired orientation of the lead 12 in the lead slot 78 and hence the lead implanted position in the brain.

In the illustrated embodiment, the clamping teeth 108 have pointed ends for improved gripping of the lead 12. In an alternative embodiment, the clamping teeth 108 have blunted ends to reduce the risk of the teeth 108 damaging the lead 12. The teeth 108 and the space between each of the adjacent teeth 108 along the respective row are sized such that the lead 12 cannot fall in between adjacent teeth 108. In this manner, the lead 12 remains gripped by the teeth 108, rather than slipping into a space between adjacent teeth 108, where gripping is less substantial and the lead 12 may thus be prone to inadvertent movement.

In the illustrated embodiment, the height of the clamping teeth 108 is substantially the same along the length of each row. In another embodiment, the height of the teeth 108 increases toward each end of the rows. This may help compensate for any skewing of the clamping bar 96 as the bar 96 is advanced toward the closed position to secure the lead 12, since the distance between the clamping bar 96 and the fixed clamping plate 84 may be greater at the respective ends if the clamping bar 96 is skewed. In another alternative embodiment, the fixed clamping bar 84 also has teeth (not shown) to help secure the lead 12, which may include the same features as those discussed above for the clamping teeth 108. Other configurations besides teeth, such as ribs, may optionally be applied.

In an alternative embodiment of the retainer 20, the retainer 20 is composed of polyether ether ketone (PEEK) material, which is highly durable and MRI-compatible. In another embodiment, the retainer 20 features exit grooves configured for seating the stimulation lead 12 bent at a ninety degree angle relative to the axis of the burr hole 6, such that the stimulation lead 12 is radially directed towards the plug base 18. In yet another alternative embodiment, the retainer 20 includes two slidable or movable clamping mechanisms, wherein each of the clamping mechanisms slide relative to the other clamping mechanism to secure the stimulation lead 12. These and other embodiments are discussed in U.S. application Ser. No. 12/258,382, which has been previously incorporated herein by reference.

Figure 21:
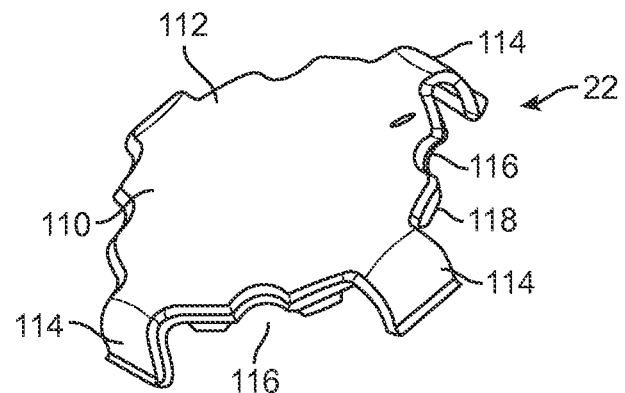
FIG. 21 is a perspective view of a cap that is part of the burr hole plug of FIG. 2.
Figure 22:
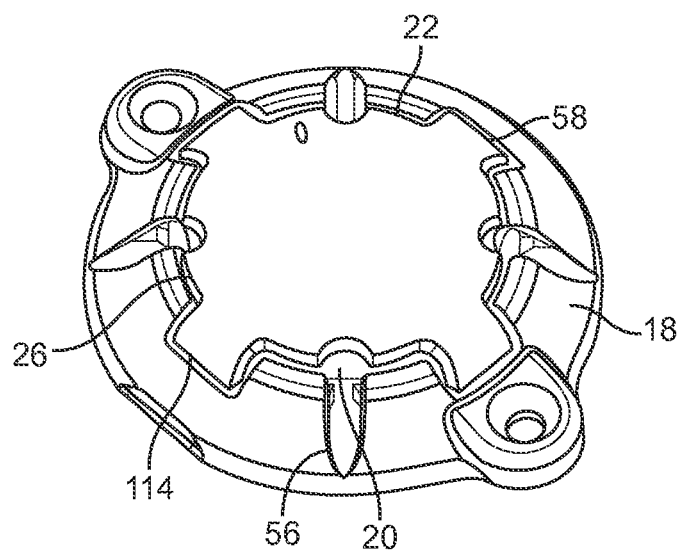
FIG. 22 is a perspective view of the cap of FIG. 21 positioned in the plug base shown in FIG. 3.

Referring to FIGS. 21 and 22, the cap or cover 22 will now be described. The cap 22 is configured for mounting to the plug base 18, particularly over the retainer 20 and over the plug base aperture 26, thereby securing the stimulation lead 12 as well as closing the burr hole 6. As mentioned above, the cap 22 may be composed of a suitable hard biocompatible material, such as titanium or a hard polymer, or may also be composed of a soft polymer, such as silastic, an elastomer, or any other combination thereof. Additionally, as mentioned above, a compressible material, such as silicone, may be applied to selected surface portions of the cap 22 to facilitate gripping by the user and/or with other burrhole device component surfaces. The cap 22 has a relatively circular lid-type body 110 and an outer rim 112 sized and shaped to be disposed within the plug base aperture 26 and to rest on the retainer 20. The cap 22 also has a plurality of winged tabs 114 that cooperate with the four wing tab recesses 54 (FIG. 3) of the plug base 18 for selectively securing the cap 22 in and releasing the cap 22 from the plug base 18. In the illustrated embodiment, the wing tabs 114 are spaced equidistantly around the outer rim 112 of the cap 22, wherein the location of the wing tabs 114 corresponds to the location of the wing tab recesses 54 of the plug base 18.

In one embodiment, the wing tabs 114 of the cap 22 may be made slightly flexible to allow for bending towards the center of the cap, while a tab is inserted into their respective corresponding tab recesses 54. In particular, one or two of the wing tabs 114 can first be inserted into their respective wing tab recesses 58, and the remaining wing tabs 114 may each be flexed inward, e.g., toward the center of the cap 22, to insert each wing tab 114 into their respective wing tab recesses 58. In an alternative embodiment, the tabs 114 are configured to flex outward, e.g., away from the center of the cap 22, to be inserted in the respective recesses 58. For example, once one tab 114 is inserted in a tab recess 58, the remaining tabs 114 may be flexed outward and over (or under) the recesses 58 in order to be positioned for insertion in the respective recesses 58.

The cap 22 also has two, three, or four cap release grooves 116 that aid in releasing the cap 22 from the plug base 18, for example, in the instance wherein a user wishes to adjust the position of the stimulation lead 12 at a subsequent time after the cap 22 has been placed over the plug base. The embodiment shown has four cap release grooves 116. The release grooves 116 are positioned about the cap 22 to correspond to the position of the channels 56 on the plug base 18. Thus, when the cap 22 is secured to the plug base 18, each cap release groove 116 and corresponding plug base channel 56 together form an opening through which a tool may be inserted to lift and release the cap 22 from the plug base 18.

Significantly, the presence of the four wing tabs 114 in the tab recesses 58 helps to control the removal of the cap 22, such that the cap is not accidentally displaced or projected. For example, in other related devices having only one corresponding tab and recess, releasing the tab from the recess may cause the cap to "pop" off, wherein the cap could land on a non-sterile surgical or operating area or an inaccessible area, or even in another area of the head of the patient. In the present embodiment, when one of the tabs 114 is disengaged from the corresponding tab recess 58, one or more of the other tabs 114 may remain in its respective recess 58, such that the cap 22 remains substantially in position relative to the retainer 18. In fact, generally, the two opposing wings tabs positioned opposite the cap release groove 116 will generally will stay in place in a hinged fashion when the tool lifts the cap at that release groove. Then, while holding the release side of cap, the side of the cap still hinged is release by lifting this side with a tool. In this manner, a user may need to release more than one tab 114 from the recesses 58 to remove the cap 22 from the plug base 18; however, this may lend to more controlled removal of the cap 22. Optionally, the cap 22 includes positioning tabs 118 that extend into the aperture 26 of the plug hole to further stabilize the position of the cap 22 during removal, as well as during insertion. While the illustrated embodiment features four corresponding tab recesses 58 and wing tabs 114, alternative embodiments may feature two, three or more tab recesses 58 and two, three or more wing tabs 114. Also, because the wing tabs 114 are uniformly configured, each tab 114 is insertable in any of the recesses 58, such that the cap 22 can be rotated and/or engaged to the plug base 18 as desired without fit issues.

Also of note, each of the combined release grooves 116 and channels 56 may accommodate the stimulation lead 12. As mentioned above, the channels 56 of the plug base 18 can receive a portion of the stimulation lead 12. When the cap 22 is secured to the plug base 18, the release grooves 116 respectively corresponding to the channels 56 also accommodate the lead 12. Thus, the lead 12 may be bent at a perpendicular angle toward the cranium 6 and maintain such position when the cap 22 is secured to the plug base 18. The combined dimensions of the release grooves 116 and corresponding channels 56 may be configured such that the lead 12 is firmly secured, e.g., by friction fit, in the selected groove 116 and channel 56. It is noted that with four total channels 56, it may be possible to implant 1, 2 or possibly 3 stimulation leads 12, and have at least one channel left to allow a tool to be inserted and lift off the cap.

Figure 23:
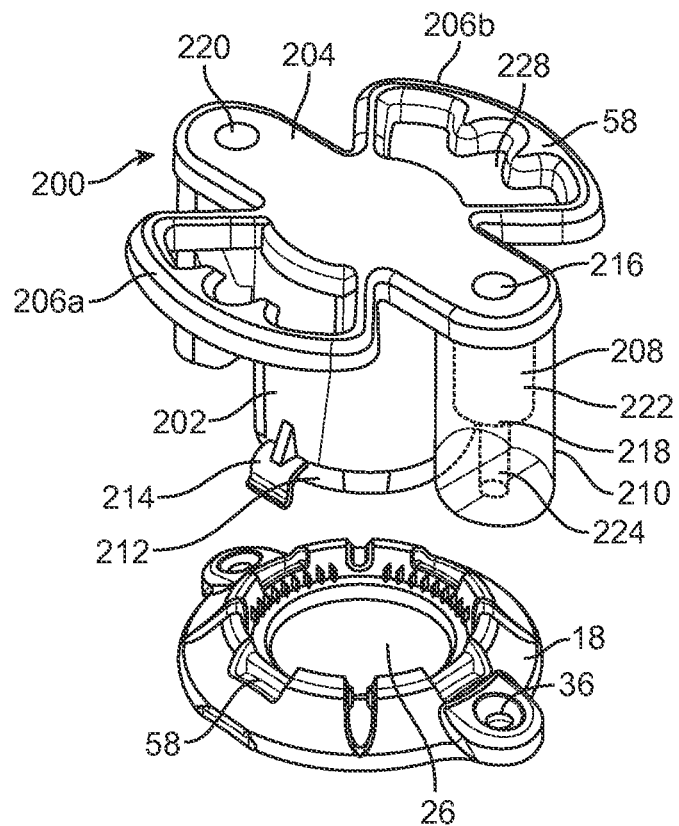
FIG. 23 is a perspective view of a plug base holding tool positioned over the plug base shown in FIG. 3.
Figure 24:
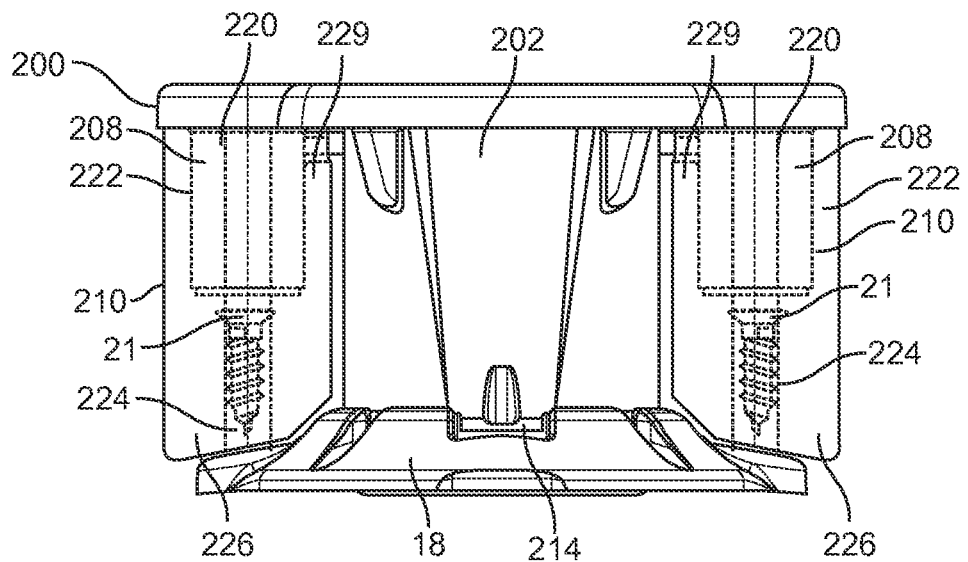
FIG. 24 is a side view of the plug base holding tool of FIG. 23 engaged to the plug base shown in FIG. 3.
Figure 25:
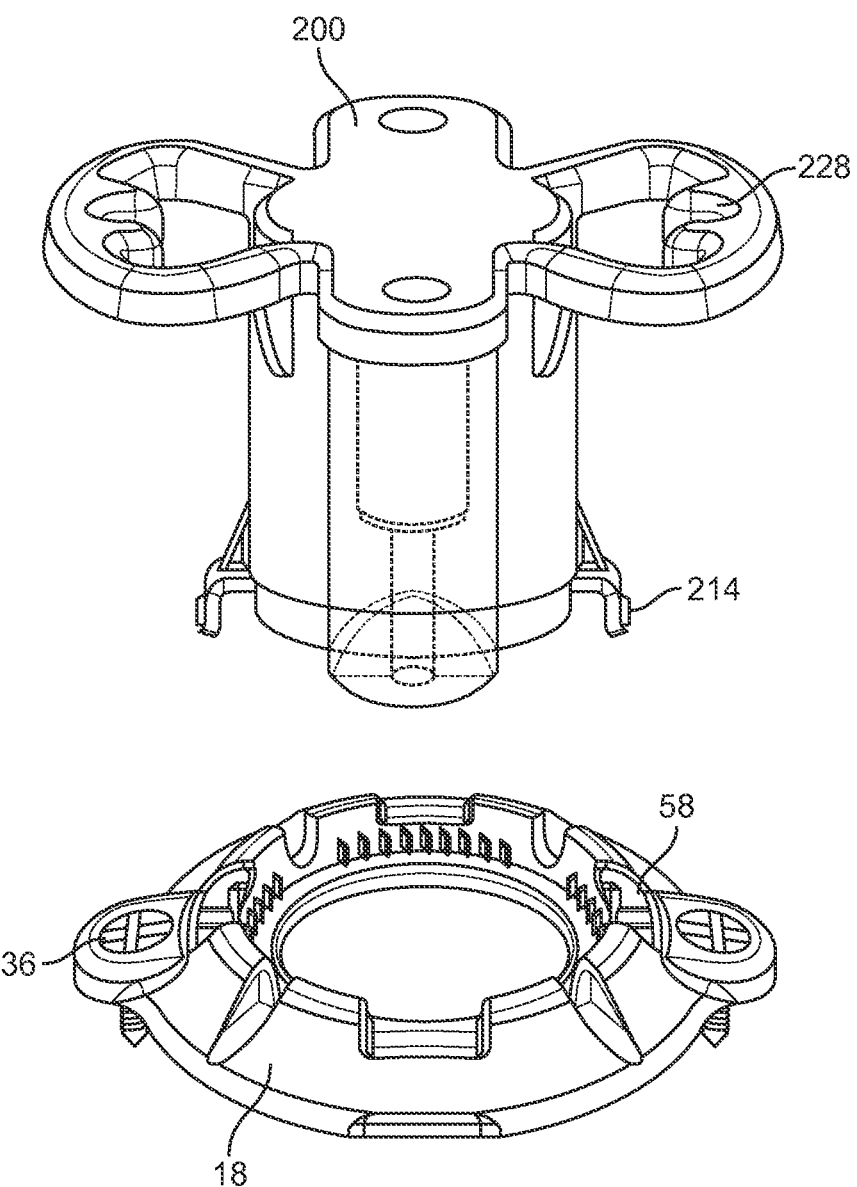
FIG. 25 is another perspective view of a plug base holding tool positioned over the plug base shown in FIG. 3 with the plug base holding tool rotated 90 degrees compared to the position in FIG. 23.
Figure 26:
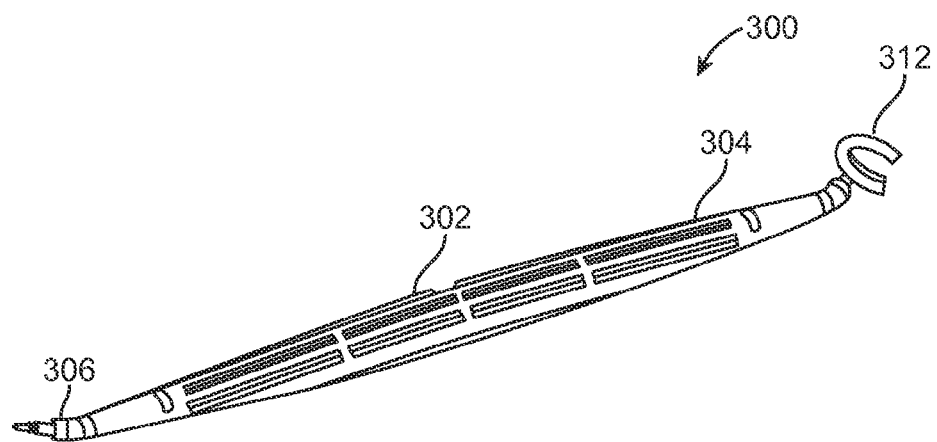
FIG. 26 is a perspective view of a retainer holding tool to be used with the burr hole plug of FIG. 2.

Referring to FIGS. 23-25, an embodiment of a plug base holding tool 200 will now be described. The plug base holding tool 200 is configured for being engaged to the plug base 18 to aid in mounting the plug base 18 to the cranium 6. The plug base holding tool 200 is used to grasp and hold the plug base and insert the plug base into the burrhole. The plug base holding tool 200 generally includes: a registration element 202; a pair of arms 204 extending from the registration element; a handle 206 mounted to the registration element 202; and a plurality of fastener receiving collars 208, each extending distally from one of the pair of arms 204. The tool 200 may be composed of a suitable rigid and robust material, such as stainless steel or a durable plastic, such as polypropylene or polycarbonate.

The registration element 202 has a cylindrical shape and an end 212 configured to be received in the plug base aperture 26. A plurality of opposing flexing holding tool tabs 214 extend from the holding tool end 212 that correspond to the position of opposing wing tab recesses 58 of the plug base 18. The tabs 214 flex to be inserted in the wing tab recesses 58 to engage the plug base 18, thus retaining the plug base holding tool 200 in position relative to the plug base 18. Notably, the flexing tabs 214 of the plug base holding tool 200 have a similar configuration to the tabs 114 of the cap 22, as both sets of tabs 22, 114 are configured for insertion in the wing tab recesses 58 of the plug base 18. In alternative embodiments, the registration element 202 may be secured in the plug base aperture 26 by other mechanisms, e.g., friction fitting or corresponding rails and recesses. Also, instead of inserting the registration element 202 in the aperture 26, the registration element 202 may be secured to an upper surface of the plug base 18 by snap fitting or other suitable mechanisms.

While the plug base holding tool 200 is secured to the plug base 18 with the tabs 214, a user may also grip the handle 206 of the tool 200 to further stabilize the tool 200 during use. The handle 206 is shaped such that the physician may ergonomically grasp it to prevent the tool 200 and the plug base 18 from moving when the plug base 18 is being anchored to the cranium 6 of the patient. The handle 206 may have any one of a variety of shapes. In the illustrated embodiment, the handle 206 has two opposing parts 206a and 206b, making a butterfly shape, thereby providing a broader base for the physician to apply a downward force on the plug base 18 or to manipulate the plug base 18 as needed. The symmetry of the handle 206 allows the downward force to be applied equally to each side of the plug base 18, thereby preventing the tool 206 and the plug base 18 from rocking back and forth. The butterfly shape of the handle 206 also prevents the physician's hand from creating an obstruction for the fastener holes 36 of the plug base 18 and allows for better viewing of the fastener holes 36 and surrounding operational area.

Notably, in the illustrated embodiment, the tabs 214 may selectively be inserted in the tab recesses 58 of the plug base 18 such that either the fastener receiving collars 208 are aligned with the fastener holes 36, or, upon a 90 degree rotation of the tool 200, that the tool alignment groove 228 is aligned with the fastener holes 36. Generally, in operating the tool 200, the tabs 214 are first inserted in the tab recesses 58 such that the fastener receiving collars 208 are aligned with the fastener holes 36 in order to insert the fasteners (generally screws) 21 in the fastener holes 36, as will be described below. Also, in the illustrated embodiment, the plug base holding tool 200 is intended to be engaged to the plug base 18 in the absence of the retainer 20 and the cap 22. In alternative embodiments, the retainer 20 and/or the cap 22 may be in position relative to the plug base 18 when the tool 200 is engaged to the plug base 18.

To receive the fasteners/screws 21, the fastener receiving collars 208 each have two openings first opening 216, and second opening 218 and a bore 220 extending between the openings 216, 218. Each collar 208 thus receives a fastener 21 in the first opening 216 and through the bore 220 and second opening 218. In the illustrated embodiment, the collars 208 are rigid to stabilize the fastener 21 and also to permit a screwdriver to be inserted into the bore 220 without undue flexing, the screwdriver used to drive the self-tapping tool into the cranium through fastener holes 36. The length of the collars 208 (shown in FIG. 24) is preferably about the length of one fastener/screw length. In addition, the entire bore length 220 is preferably about two screw lengths as shown in FIG. 24. It can be seen that the length of the bore 220 should be longer than a single screw length in order to permit the tip of a screwdriver to be placed in the bore such the bore helps stabilize the tip of the screwdriver while it is being turned to drive the screw into the cranium.

In the embodiment shown, the tool 200 also has two fastener retention receptacles 210 covering the respective two fastener receiving collars 208, wherein each receptacle 210 contains or covers a collar 208 and may receive a fastener/screw 21 in the bottom 224 of the bore 220. The fastener retention receptacles 210 are made from a transparent or translucent material, such as implantable grade silicone rubber or a semi-hard polymer, which material permits the viewing of the location of the fasteners/screw 21 in the receptacles 210. Each receptacle 210 has a first bore 222 configured for receiving one of the collars 208 and a second bore 224 configured for receiving the fastener/screw 21. In the illustrated embodiment, the first bore 222 is slid over the collar 208. The receptacle 210 can be slid over a substantial length or the entire length of the collar 208 and be snugly fit over the collar 208. The receptacle 210 may also be selectively slid on and off the collar 208. In alternative embodiments, the receptacle 210 may be permanently affixed to the collar 208 at a point along the length of the collar 208 or to a distal end of the collar 208.

Each receptacle 210 has an end 226 with one or more surfaces having geometries that correspond to the configuration of the top surface 28 of the plug base 18. The ends 226 of the receptacles 210 may be abutted to the plug base 18 to provide a seamless travel path for the screw to go through between the second bore 224 and the fastener hole 36 in the plug base 18. Each receptacle 210 has a key 229. that serves as a visual marker for correctly aligning the end 226 of each receptacle 210 with the corresponding configuration of the top surface 28 of the plug base 18. In the illustrated embodiment, each key 229 is positioned to be directly facing the registration element 202 when the receptacle 208 is properly aligned over the plug base 18. Typically, the key 229 is used as a visual marker during manufacture and assembly, but the key 229 may also be referred to as needed for any adjustment of the receptacles 210 as performed by the user.

As mentioned above, the bore 224 of the receptacle 210 receives the fastener 21/screw as it exits through the opening 218 of the fastener receiving collar 208. In the illustrated embodiment, the length of the second bore 224 is approximately about or slightly greater than the length of the fastener/screw 21. Also, the diameter of the second bore 224 is preferably slightly smaller than the largest diameter of the fastener 21, e.g., a screw head, such that the fastener/screw 21 is held in place by the slightly compressible wall of the second bore 224, while the screw is being turned and driven into the cranium. The compressibility of the receptacle 210 material allows for controlled movement of the fastener 21 through the distal bore 224 when a displacing force is applied, e.g., when a screwdriver is used to drive the screw/fastener through the bore 224. In the illustrated embodiment, the distal bore 224 is tapered to further control movement of the fastener 21.

The alignment of the receptacles 210 with the fastener holes 36, and the controlled movement imparted by the receptacles 210 on the fasteners/screws 21, help to ensure that the fasteners/screws 21 are properly inserted in the fastener holes 36. This design limits the possibility of a fastener/screw 21 falling out of the fastener hole 36, and ensures that the fastener/screw is placed without skewing into the cranium.

Notably, the fastener receiving collars 208 and the fastener retention receptacles 210 are each formed from a singled molded component. If these components were formed from separate parts, the components could undesirably shift, separate or deform while a screwdriver is placed in the bores 220 and 224. In an alternative embodiment, rather than the fastener/screw receiving collars 208 and the fastener retention receptacles 210 being molded as individual components, the fastener receiving collars 208 and the fastener retention receptacles 210 may be molded together as a single component.

In addition to aligning the fasteners/screws 21 with the fastener holes 36 and stabilizing the fasteners 21, the plug base holding tool 200 also allows for pre-positioning the fasteners 21 in the fastener retention receptacles 210. Specifically, during manufacture, each fastener/screw 21 can be inserted through a fastener receiving collar 208 and into the distal bore 224 of a fastener retention receptacle 210 and remain in the distal bore 224 through shipping and until use. The secure fit of the fasteners/screws 21 in the receptacle 210, particularly in the compressible material, helps to ensure the fasteners/screws 21 remain in position during shipping and storage. Also, the compressible material of the receptacles 210 dampens vibrations during shipping, further preventing movement of the fasteners 21, and the transparency of the receptacles 210 allows for viewing to ensure the fasteners 21 are properly positioned. Thus, when the user is ready to drive the fasteners/screws 21 in the cranium 6, the user only needs to insert a screwdriver through the fastener receiving collars 208 to access the fasteners/screws 21 in the receptacles 210. The user may then advance the fasteners/screws 21 from the receptacles 210 directly into the fastener holes 36 and into the cranium 6.

After the fasteners/screws 21 are inserted through the fastener holes 36 and into the cranium 6, the handle 206 of the plug base holding tool 200 may be used to ensure the fasteners 21 are fully secured in the cranium 6. Specifically, each wing of the handle 206 has a tool alignment groove 228 to support the fastener tool (e.g., screwdriver) and align the fastener tool with the fasteners 21. To this end, the flexing tabs 214 are disengaged from the tab recesses 58 of the plug base 18, for example, by using the retainer holding tool which will be described further below, to release the plug base holding tool 200 from the plug base 18. Upon release, the plug base holding tool 200 is rotated 90 degrees to insert the tabs 214 in the corresponding tab recesses 58 and re-engage the plug base holding tool 200 with the plug base 18, as shown in FIG. 25. In this configuration, the wings of the handle 206, and particularly the tool alignment grooves 228, are aligned vertically with the fastener holes 36, such that the screwdriver shaft may be placed in the grooves 228 to further tighten the fasteners 21 into the cranium 6. The grooves 228 help ensure that the screwdriver is properly aligned with the fasteners/screws 21 to prevent skewing of the fasteners/screws 21 or stripping of the plug base 18.

Of note, in the illustrated embodiment, the handle 206 extends from the top end of the registration element 202. In an alternative embodiment, the handle 206 may extend from a bottom or central section of the registration element 202. In another alternative embodiment, the handle 206 may have other configurations besides open wings, such as an oblong configuration. These and other embodiments are referred to in U.S. application Ser. No. 12/258,382, which has been previously incorporated herein by reference.

Referring to FIGS. 26-33, a retainer holding tool 300 will now be described. The retainer holding tool 300 performs multiple operations, including positioning the retainer 20 within the aperture 26 of the plug base 18 and removing the cap 22 from the plug base 18. In particular, the retainer holding tool 300 generally includes a handle 302, a gripping end 304, and an insertion end 306, wherein the gripping end 304 and the insertion end 306 are on opposing ends of the handle 302. The gripping end 304 is used to grip and position the retainer 20 within the aperture 26 of the plug base 18, while the insertion end 306 is used for insertion in various components of the burr hole plug 16 for manipulating such components, including moving the movable parts of the retainer 20 or releasing parts from another part using the insertion end 306.

The gripping end 304 of the retainer holding tool 300 includes a metal pin 308 extending through the handle 302 with a collar 310 mounted on the pin 308. A C-shaped flange 312 is mounted on the collar 310 and has and two pegs 314, 316, one located on one end of the C-shaped flange 312 and the other one located near the center of the C-shaped flange 312. Optionally, a third peg (not shown) can be provided on the other end of the C-shaped flange 312. The handle 302 is used to manipulate the gripping end 304 to position the C-shaped flange 312 onto the retainer 20 and then place the retainer 20 in the recess 26 of the plug base 18. Also, the C-shaped configuration of flange 312 accommodates the stimulation lead 12 exiting the burr hole 5 while the retainer 20 is positioned in the plug base 18. Specifically, the C-shaped flange 312 extends around the retainer 20 without obstructing the lead slot 76, and the lead 12.

The C-shaped flange 312 and/or collar 310 is generally composed of a rigid material such as stainless steel, or a durable plastic such as polypropylene or polycarbonate. Selected surfaces of the C-shaped flange 312 may also be coated with silicone to improve gripping interaction between the C-shaped flange 312 and other components. The silicone coating also allows for the C-shaped flange 312 to be used with a wider range of dimensions, since the compressibility and added width of the silicone permits gripping of surfaces in areas that may otherwise to be too small or too large for accommodating the C-shaped flange 312.

The pegs 314, 316 are spaced from each other, such that they engage with contact points, particularly corresponding recesses or holes, on the flat retainer disk 66. The pegs 314, 316 are positioned such that they are insertable in corresponding features on the disk 66 of the retainer 20 in an interference arrangement, e.g., a frictional fit, to hold the retainer 20 and position it to the plug base 18. Specifically, one peg 314 is insertable through the keyhole recess 80 of the retainer 20, and another peg 316 is insertable through the sliding recess 86 of the retainer 20. Of note, the pegs 314, 316 engage the base disk 66 on a side opposite to where the clamping mechanism 76 is positioned. This ensures that the retainer 20 is not inserted upside-down in the plug base 18.

The retention force exerted between the pegs 314, 316 and the retainer 20 should be less than the retention force exerted between the retainer 20 and the plug base 18 once the retainer is inserted in the plug base, so that when the tool 300 is pulled, it will easily detach from the retainer 20 leaving it inserted into the plug base 18. To accomplish this, the spacing between the pegs 314, 316 may be slightly less than the spacing between the recesses 80, 86 to provide a slight, spring, compressive inward force between the pegs, when the pegs are inserted into the recesses. Additionally, the C-shaped flange 312 may be biased inwardly (i.e., the ends of the "C" are biased toward the center of the "C"). In an alternative embodiment, the pegs 314, 316 are configured with separation distance that is slightly larger than the distance between the two recesses 80, 86, so that the arms of the C-shaped flange push outwardly from the center and thereby hold the retainer 20. In another alternative embodiment, to strengthen the interference fit, the pegs 314, 316 may include barbs (not shown).

In one embodiment, the tool 300 includes a support tab (not shown) located on the end of the C-shaped flange 312 opposite the peg 314, thereby facilitating the application of uniform pressure on the disk base 66 when the tool 300 positions the retainer 20 within the plug base aperture 26.

The collar 310 is mounted on the metal pin 308 such that the collar 310, and the C-shaped flange 312 mounted thereon are rotatable about the pin 308. The rotational feature of the C-shaped flange 312 allows for the flange 312 to be positioned as needed for receiving the lead 12 in the open center of the flange 312, so as not to interfere with the position of the lead 12. The collar 310 also has a friction fit with the pin 308 such that the collar 310 and flange 312 may only be rotated with the application of force (e.g., from the user), rather than allowing the collar 310 and flange 312 to freely rotate.

The metal pin 308 includes a reduced diameter boss 318 with a barb 320 that is received within the collar 310 and configured to form an interference-fit in the collar 310 to prevent the C-shaped flange 312 from separating from the tool 300 during use. However, the C-shaped flange 312 may also be separated from the pin 308 with the application of sufficient force to overcome the interference fit between the boss 318 and the collar 310. In one embodiment, a movable pin (not shown) is disposed within a side wall of the collar 310, and the boss 318 has an annular recess (not shown) that receives the movable pin. The movable pin slides with the annular recess, thereby allowing the collar 310, and thus, the C-shaped flange 312, to rotate about the axis of the handle 302.

Figure 30:
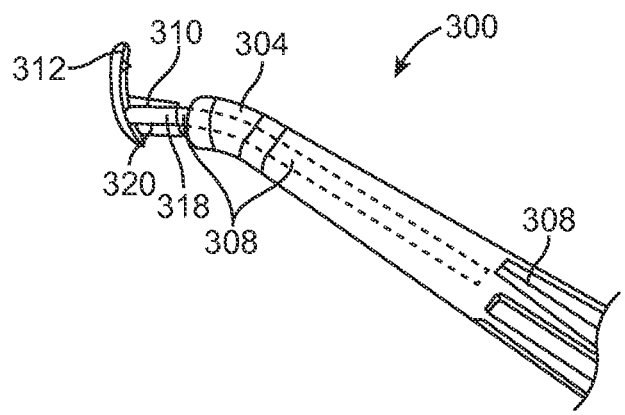
FIG. 30 is a perspective, sectional view of the end of the retainer holding tool shown in FIG. 29.
Figure 31:
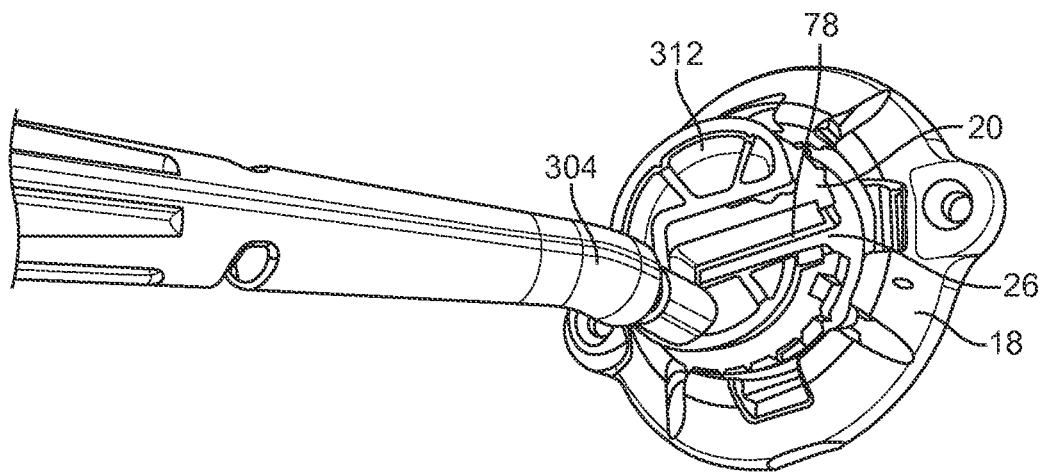
FIG. 31 is a perspective view of the end of the retainer holding tool shown in FIG. 29 used with the retainer of FIG. 11 and the plug base of FIG. 3.

The metal pin 308 is fixed in position within the handle 302 and preferably extends through a length of the handle 302, as best seen in FIG. 30. Otherwise, for a metal pin of shorter length, there could be an increased risk of the pin falling out of the handle. The metal pin 308 may be secured in the handle 302 with adhesive, by friction fit, by a mechanical fastener, or other suitable mechanisms. In another embodiment, the pin 308 is molded with the handle 302, instead of being a separate component that is secured to the handle 302, and may be formed of the same material as the handle, e.g., plastic.

The handle 302 is bent at the gripping end 304, such that the C-shaped flange 312 is angled relative to the handle 302 to facilitate manipulation of the retainer 20 in tight spaces and around other parts. Thus, the handle 302 does not obstruct the view of C-shaped flange and the burrhole while the tool 300 is being used. In one embodiment, the handle 302 may be made of material that is relatively malleable to allow the physician to selectively bend the handle 302 to achieve the desired angle.

In another embodiment, a retainer holding tool (not shown) comprising a handle and a plurality of fingers is used for positioning the retainer 20 within the aperture 26 of the plug base 18. The fingers are preferably curved and extend from the handle 432 to engage a surface of the retainer. This and other embodiments are referred to in U.S. application Ser. No. 12/258,382, which has been previously incorporated herein by reference.

Figures 27, 28:
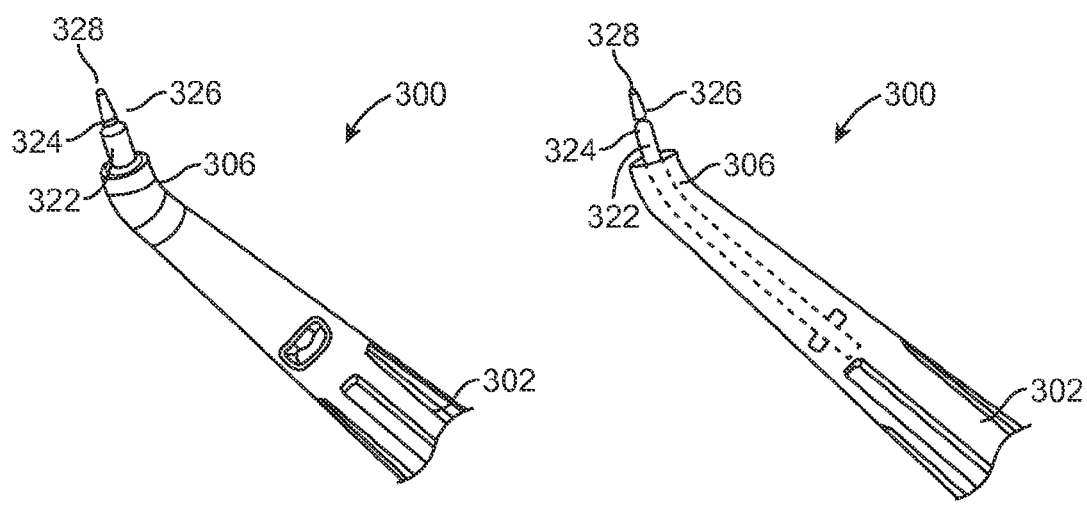
FIG. 27 is a perspective view of one end of the retainer holding tool of FIG. 26.
FIG. 28 is a perspective, sectional view of the end of the retainer holding tool shown in FIG. 27.
Figure 29:
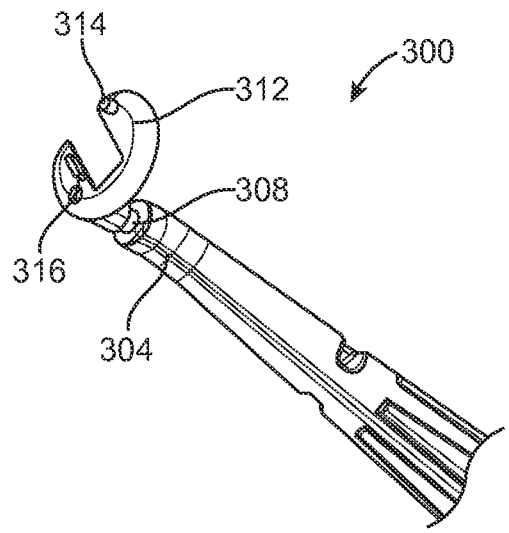
FIG. 29 is a perspective view of another end of the retainer holding tool of FIG. 26.

Now to describe the insertion end 306 of the tool 300, the insertion end 306 includes a metal pin 322, which further includes a notch 324, an annular securing ring 326, and a tapered end 328. Similar to the metal pin 308 of the gripping end 304, the metal pin 322 of the insertion end 306 is fixed in position within the handle 302 and extends through a substantial length of the handle 302, as best seen in FIG. 28. The metal pin 322 at the insertion end of tool 300 may be secured in the handle 302 with adhesive, by friction fit, by a mechanical fastener, or other suitable mechanisms. In another embodiment, the pin 322 is molded with the handle 302, instead of being a separate component that is secured to the handle 302, and may be formed of the same material as the handle, e.g., plastic. Also similar to the gripping end 304, the handle 302 may optionally be made of malleable material that allows it to be bent at the insertion end 306 to facilitate manipulation of the pin 322 in tight spaces and around other parts. The end of the pin 322 is blunted to minimize the risk of damage to burr hole plug 16 components, surgical gloves and/or the user.

Figure 32:
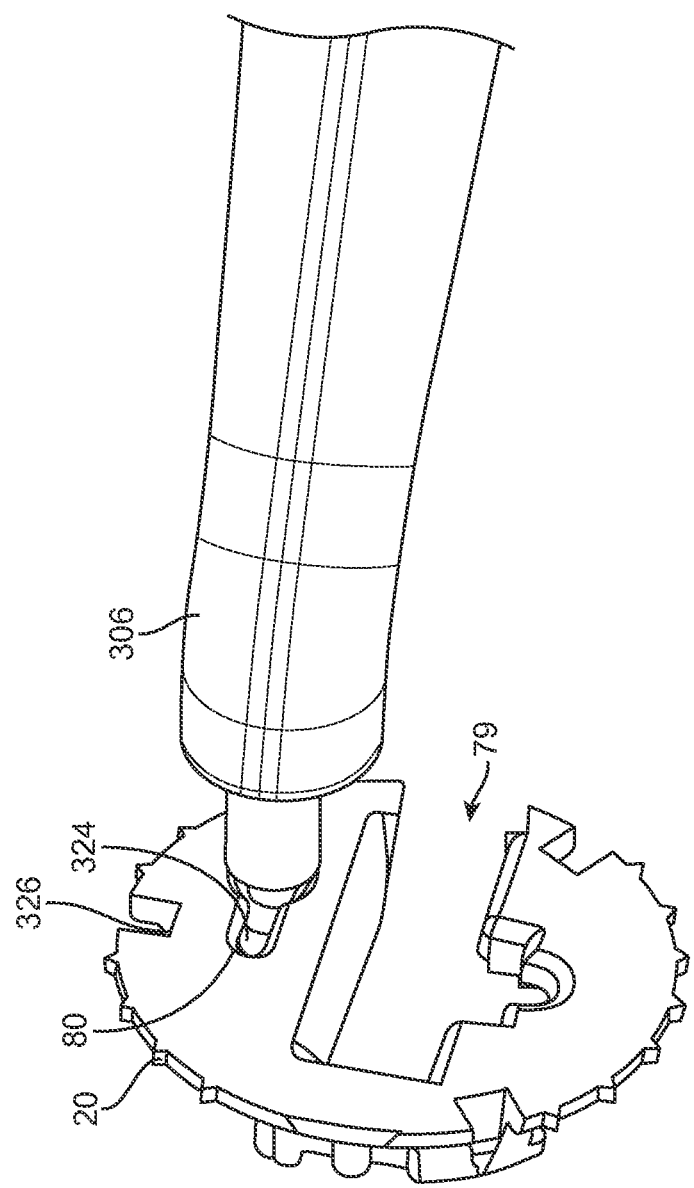
FIG. 32 is a perspective view of the end of the retainer holding tool shown in FIG. 27 used in engaging the retainer of FIG. 11.

The insertion end 306 is used to manipulate the retainer 20 with respect to the plug base 18. Specifically, the metal pin 322 of the insertion end 306 can be inserted in the operating recess 109 to flex the cantilever arm 103 and to move the clamping mechanism 76, e.g., between the open and closed positions. The metal pin 322 can also be inserted into the keyhole recess 80 of the retainer 20, as shown in FIG. 32, to attach the retainer 20 and allow it to be removed from the plug base 18. In particular, the notch 324 and the annular securing ring 326 are inserted through the keyhole recess 80, wherein the securing ring 326 has a diameter slightly larger than the diameter of the keyhole recess 80, so that when the securing ring 326 is inserted into the keyhole recess 80, the retainer becomes attached to the metal pin by a snap fit. Also, the notch 324 allows the metal pin 322 to slide in the keyhole recess 80 for positioning the metal pin 322 in the keyhole recess 80 as desired. To release the metal pin from the retainer, the handle is used as a lever to pop the metal off from the retainer. In addition, to remove the retainer, the metal pin may be inserted into the keyhole recess 80, and the handle may be used as a lever to pop off the retainer from the plug base.

Figure 33:
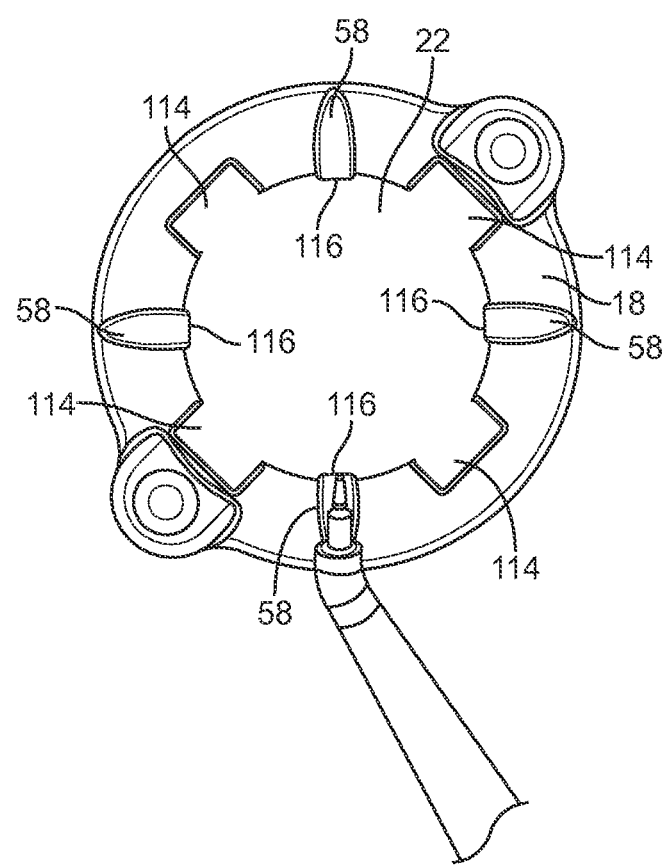
FIG. 33 is a perspective view of the end of the retainer holding tool shown in FIG. 27 used with the plug base of FIG. 3 and the cap of FIG. 21.

The insertion end 306 of the tool 300 can also be used to place and remove the cap 22 from the plug base 18. To place the cap 22 onto the plug base, the pin 322 may be used to push, i.e., flex, the tabs 114 of the cap 22 inward for insertion in the tab recesses 58 of the plug base 18. To remove the cap 22 from the plug base 18, the metal pin 322 may be inserted into any one of the release grooves 116 of the cap 22, along with the respective channel 56 of the retainer 20 adjacent thereto, as shown in FIG. 33. When the handle 302 is used to apply a leveraging force to the pin 322 in the selected corresponding channel 56 and release groove 116, the pin 322 causes one or more of the tabs 114 of the cap 22 to disengage and be released from the respective tab recess(es) 58 of the plug base 18. Once the tabs 114 of the cap 22 are released from the tab recesses 58 of the plug base 18, the cap 22 may be removed from the plug base 18.

In an alternative embodiment, instead of a tapered pin 322, the insertion end 306 features a linear shaft extending from the handle 302 that terminates in a ball configuration.

The methods for mounting the burr hole plug 16, as described above, into the burr hole 5 are generally described in U.S. application Ser. No. 12/258,382, which has been previously incorporated herein by reference. Methods for using the tools described above with the burr hole plug 16 are also described in the incorporated reference.

Although particular embodiments of the present inventions have been shown and described, it will be understood that it is not intended to limit the present inventions to the preferred embodiments, and it will be obvious to those skilled in the art that various changes and modifications may be made without departing from the spirit and scope of the present inventions. Thus, the present inventions are intended to cover alternatives, modifications, and equivalents, which may be included within the spirit and scope of the present inventions as defined by the claims.

The invention claimed is:

1. A holding tool that cooperates with a cranial burr hole plug having an aperture and a fastener hole for respectively receiving a fastener to secure the burr hole plug to a cranium, comprising:
    a registration element configured for being inserted into the aperture of the burr hole plug;
    a rigid collar affixed to the registration element for receiving the fastener, the rigid collar including a first bore that is in a coaxial relationship with the fastener hole when the registration element is inserted into the aperture of the burr hole plug;
    a flexible receptacle including a second bore having an enlarged bore portion in which the rigid collar is positioned and a narrow bore portion in a coaxial relationship with the first bore of the rigid collar for receiving the fastener as it exits the collar, the narrow bore portion having a relaxed diameter smaller than the largest diameter of the fastener.

2. The holding tool of claim 1, wherein the receptacle is transparent.

3. The holding tool of claim 1, wherein the receptacle is composed of silicone.

4. The holding tool of claim 1, wherein the narrow bore portion is configured to receive and maintain the fastener in position prior to applying a force to secure the burr hole plug to the cranium.

5. The holding tool of claim 1, wherein a length of the narrow bore portion is at least as long as a length of the respective fastener received therein.

6. The holding tool of claim 1, wherein the burr hole plug comprises a plurality of recesses, and wherein the tool further comprises a plurality of tabs that engage the recesses of the burr hole plug to secure the tool to the burr hole plug.

7. The holding tool of claim 1, further comprising a handle having an aperture configured to selectively align with the fastener hole, wherein the aperture is configured to receive a tool for maneuvering a fastener received in the fastener hole.

8. The holding tool of claim 7, wherein the holding tool is selectively rotatable to selectively align the handle aperture or the receptacle with the fastener hole of the burr hole plug.

9. The holding tool of claim 7, wherein the handle has a winged configuration.

10. The holding tool of claim 1, wherein the receptacle has a unibody configuration.

11. The holding tool of claim 1, wherein the cranial burr hole has another fastener hole diametrically disposed opposite to the fastener hole for respectively receiving another fastener to secure the burr hole plug to the cranium, comprising:

- another rigid collar affixed to the registration element for receiving the fastener, the other rigid collar being diametrically disposed opposite to the rigid collar, the other rigid collar including a third bore that is in a coaxial relationship with the other fastener hole when the registration element is inserted into the aperture of the burr hole plug;
- another flexible receptacle including a fourth bore having an enlarged bore portion in which the rigid collar is positioned and a narrow bore portion in a coaxial relationship with the third bore of the other rigid collar for receiving the other fastener from the other collar, the narrow bore portion having a relaxed diameter smaller than the largest diameter of the other fastener.

12. The holding tool of claim 1, further comprising the fastener.

13. The holding tool of claim 12, wherein the fastener is a screw.

* * * * *